(12) United States Patent
Wolf et al.

(10) Patent No.: US 10,974,004 B2
(45) Date of Patent: Apr. 13, 2021

(54) AUTOMATIC ULTRASOUND TITRATION OF CONTINUOUS POSITIVE AIRWAY PRESSURE (CPAP) TREATMENT FOR SLEEP APNEA

(71) Applicants: University Of Maryland, Baltimore, Baltimore, MD (US); Board of Regents, The University of Texas System, Austin, TX (US)

(72) Inventors: Jeffrey S. Wolf, Owings Mills, MD (US); Amal Isaiah, Hanover, MD (US)

(73) Assignees: University Of Maryland, Baltimore, Baltimore, MD (US); Board of Regents, The University of Texas System, Austin, TX (US)

( * ) Notice: Subject to any disclaimer, the term of this patent is extended or adjusted under 35 U.S.C. 154(b) by 275 days.

(21) Appl. No.: 16/075,687

(22) PCT Filed: Feb. 2, 2017

(86) PCT No.: PCT/US2017/016192
§ 371 (c)(1),
(2) Date: Aug. 6, 2018

(87) PCT Pub. No.: WO2017/136535
PCT Pub. Date: Aug. 10, 2017

(65) Prior Publication Data
US 2020/0038609 A1    Feb. 6, 2020

Related U.S. Application Data

(60) Provisional application No. 62/291,937, filed on Feb. 5, 2016.

(51) Int. Cl.
*A61M 16/00*    (2006.01)
*A61M 16/06*    (2006.01)
(Continued)

(52) U.S. Cl.
CPC ......... *A61M 16/024* (2017.08); *A61B 8/4488* (2013.01); *A61B 8/5223* (2013.01);
(Continued)

(58) Field of Classification Search
CPC .. A61B 8/4488; A61B 8/5223; A61M 16/024; A61M 16/06; A61M 2205/3344; A61M 2205/3375; A61M 2205/502
(Continued)

(56) References Cited

U.S. PATENT DOCUMENTS 8,187,201 B2    5/2012    Lynn
9,430,701 B2 *  8/2016    Roy .................... G06K 9/4638
(Continued)

OTHER PUBLICATIONS

International Search Report and Written Opinion for correspondence PCT Application PCT/US17/16192 dated Apr. 17, 2017, pp. 1-11.
(Continued)

*Primary Examiner* — Navin Natnithithadha
(74) *Attorney, Agent, or Firm* — Wolter Van Dyke Davis, PLLC; Eugene J. Molinelli

(57) ABSTRACT

Techniques for automated titration of CPAP device for a subject include receiving multiple ultrasound images representing a cross section of an airway in a neck of the subject at corresponding different times. Multiple different positive pressure values imposed by a device on the airway of the subject are also received at each of the corresponding times. For each of the ultrasound images, a mask of pixels associated with an air-tissue interface is automatically formed, and a value of a statistic of pixels within the mask is automatically determined. A titration pressure for a continuous positive airway pressure (CPAP) device is automatically determined based on the positive pressures and the value of the statistic for each of the ultrasound images. Output data that indicates the titration pressure for the CPAP device is
(Continued)

presented on a display device, such as by operating the CPAP device itself at the titration pressure.

8 Claims, 14 Drawing Sheets

(51) Int. Cl.
   *A61B 8/00* (2006.01)
   *A61B 8/08* (2006.01)
(52) U.S. Cl.
   CPC ..... *A61M 16/06* (2013.01); *A61M 2205/3344* (2013.01); *A61M 2205/3375* (2013.01); *A61M 2205/502* (2013.01)
(58) Field of Classification Search
   USPC ............ 128/204.23; 600/529–543, 484, 443, 600/438, 437, 449
   See application file for complete search history.

(56) References Cited

U.S. PATENT DOCUMENTS

| | | | |
|---|---|---|---|
| 9,679,375 | B2* | 6/2017 | Eskandari ............ A61B 8/5269 |
| 2013/0046181 | A1 | 2/2013 | Al-Abed et al. |
| 2015/0209001 | A1 | 7/2015 | Wolf et al. |
| 2015/0227784 | A1* | 8/2015 | Roy .................. G06K 9/00201 382/103 |
| 2017/0061607 | A1* | 3/2017 | Eskandari ................ G06T 5/30 |
| 2017/0160171 | A1* | 6/2017 | Tsujikawa ............ G06T 7/0012 |

OTHER PUBLICATIONS

Clement G, et al., 2000., "Investigation of a large-area phased array for focused ultrasound surgery through the skull", Physics in Medicine and Biology, vol. 45, pp. 1071-1083.

Collop N, et al, 2007, "Clinical guidelines for the use of unattended portable monitors in the diagnosis of obstructive sleep apnea in adult subjects", J Clin Sleep Med, vol. 3, pp. 737-747.

Deberry-Borowiecki, B., et al, 1988, "Cephalometric analysis fordiagnosis and treatment of obstructive sleep apnea", Laryngoscope, vol. 98, pp. 226-234.

Ezri T, et al, 2003, "Prediction of difficult laryngoscopy in obese subjects by ultrasound quantification of anterior neck soft tissue", Anaesthesia, vol. 58, pp. 1111-1114.

Girard, E, 2003, "Automated Detection of Obstructive Sleep Apnea Using Ultrasound Imaging" Charlottesville, Va.: University of Virginia, pp. 1-79.

Hoskins P., et al, 2010, "Diagnostic ultrasound: physics and equipment", Cambridge, U.K.: Cambridge University Press, Chapter 3 pp. 23-46, Chapter 12 pp. 155-170.

Kajekar P., et al, 2010, "Role of Ultrasound in Airway Assessment and Management", International J Ultrasound & Applied Technologies in Perioperative Care, pp. 97-100.

McNay M., et al, 1999, "Forty years of obstetric ultrasound 1957-1997: From A-scope to three dimensions" Ultrasound in Medicine and Biology, vol. 25, pp. 3-56.

Riley R, et al, 1985, "Palatopharyngoplasty failure, cephalometric roentgenograms, and obstructive sleep apnea", Otolaryngology—Head and Neck Surgery, vol. 93, pp. 240-243.

Riley R, et al, 1993, "Obstructive sleep apnea syndrome: a review of 306 consecutively treated surgical subjects" Otolaryngology—Head and Neck Surgery, vol. 108, pp. 117-125.

Shepard J., et al, 1990, "Localization of upper airway collapse during sleep in subjects with obstructive sleep apnea", American Journal of Respiratory and Critical Care Medicine, vol. 141, pp. 1350-1355.

Siegel H, et al, 2000, "Obstructive sleep apnea: a study by simultaneous polysomnography and ultrasonic imaging", Neurology, vol. 54, pp. 1872-1872.

Smith S, et al, 1986, "Phased array ultrasound imaging through planar tissue layers" Ultrasound in Medicine & Biology, vol. 12, pp. 229-243.

Veasey S., et al, 2006, "Medical therapy for obstructive sleep apnea: a review by the Medical Therapy for Obstructive Sleep Apnea Task Force of the Standards of Practice Committee of the American Academy of Sleep Medicine", Sleep, vol. 29, Issue 8, pp. 1036-1044.

International Search Report and Written Opinion, International patent Application No. PCT/US2017/16192 dated Apr. 17, 2017; pp. 4-11.

* cited by examiner

FIG. 5A  FIG. 5B  FIG. 5C
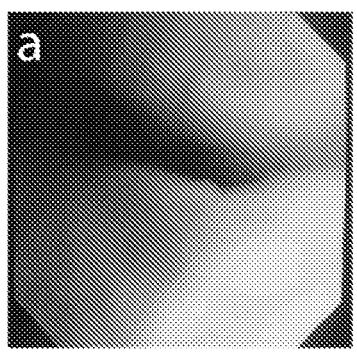
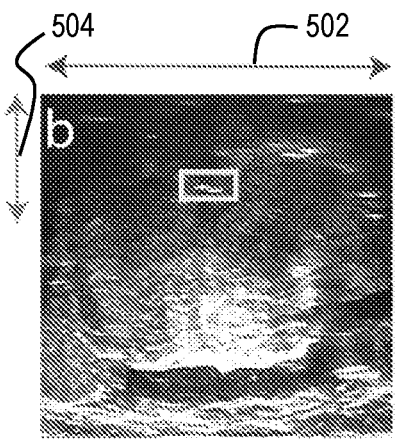
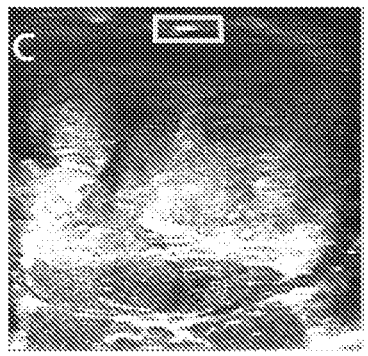
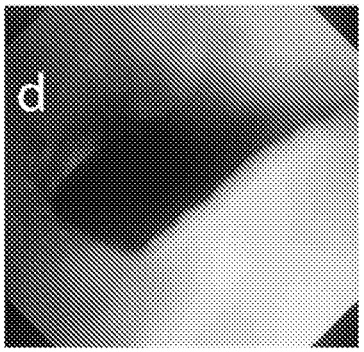
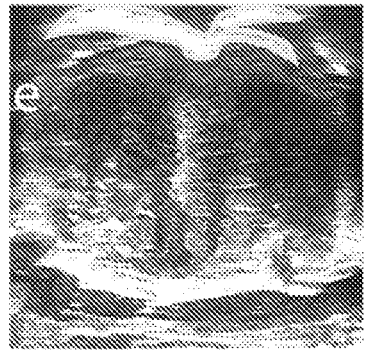
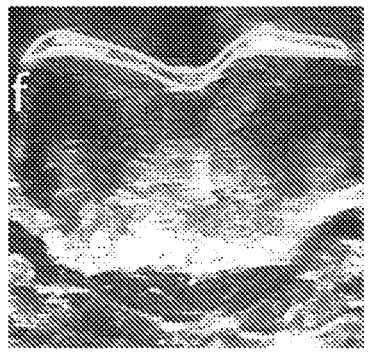
FIG. 5D  FIG. 5E  FIG. 5F

FIG. 7A  FIG. 7B  FIG. 7C  FIG. 7D

AUTOMATIC ULTRASOUND TITRATION OF CONTINUOUS POSITIVE AIRWAY PRESSURE (CPAP) TREATMENT FOR SLEEP APNEA

CROSS-REFERENCE TO RELATED APPLICATIONS

This application is a 371 national stage application of PCT Application No. PCT/US17/16192, filed Feb. 2, 2017, and claims benefit of Provisional Appln. 62/291,937, filed Feb. 5, 2016, the entire contents of which are hereby incorporated by reference as if fully set forth herein, under 35 U.S.C. § 119(e).

BACKGROUND

Obstructive sleep apnea (OSA) syndrome occurs with an estimated prevalence of 2-9% in adult American population with an increasing incidence (Strollo et al. 1996; Shamsuzzaman et al. 2003). OSA has been recognized as a major cause of morbidity in recent years. The condition is firmly seated within a spectrum of sleep-related breathing disorders (Flemons 2002), including snoring, upper airway resistance syndrome and obesity-hypoventilation syndrome. Left untreated, OSA can manifest in conditions with significant detriment to quality of life: daytime sleepiness (Johns 1993) and cognitive impairment (Findley et al. 1986). More significantly untreated OSA leads to increased morbidity and mortality from systemic and pulmonary hypertension (Marin et al. 2005), myocardial infarction (Hung et al. 1993), cardiac arrhythmias (Guilleminault et al. 1983), stroke and an increased risk of motor vehicle accidents (Teran-Santos et al. 1999). Given these implications, accurate and early diagnosis of OSA can potentially benefit early interventions to halt initiation and progression of cardiovascular diseases. However, due to the lack of consensus regarding specific diagnostic tools and criteria, most of the subjects with OSA remain untreated and the management of complications adds to the burden of healthcare costs.

Obstructive events occur when tissue in the upper airway collapses during sleep. This occurs during the negative pressure environment of inspiration. The exact sites of collapse vary in each person depending on their anatomy and to date there is no acceptable mechanism to predict or identify site of obstruction.

Treatment for sleep apnea events include continuous positive airway pressure (CPAP) provided by a CPAP device. The process to determine the positive pressure to keep an airway open is called CPAP titration. A CPAP titration study will typically follow an in lab diagnostic study for sleep apnea. The titration study itself is done in a lab and is for the purposes of calibrating a CPAP machine to ensure CPAP therapy is successful at keeping the airway open and preventing a sleep apnea event.

SUMMARY

Techniques are provided for the automatic collection of ultrasound imaging data for titration of a CPAP device. In some embodiments the techniques automate the determination of airway patency (openness) and can be used for localization of an obstruction contributing to obstructive sleep apnea. Ultrasound is defined as pressure waves in a medium at frequencies higher than those detectable by normal human auditory systems, and includes frequencies from about 20 kilohertz (kHz, 1 kHz=$10^3$ Hertz, 1 Hertz, Hz, is one cycle per second) up to about several gigahertz (GHz, 1 GHz=$10^9$ Hertz). For use in non-invasive imaging of human tissues to practical depths of tens of centimeters (cm, 1 cm=$10^{-2}$ meters) ultrasound frequencies in the range from about 2 to 100 megahertz (MHz, 1 MHz=$10^6$ Hertz) are used. To avoid heating and destructive effects, the power area density of such ultrasound waves is less than about 1 watt per square centimeter (Wcm$^{-2}$).

In a first set of embodiments, a method includes automatically receiving multiple ultrasound images representing a cross section of an airway in a neck of a subject obtained by an ultrasound transducer array directed toward the subject at a corresponding plurality of different times; and, automatically receiving multiple different positive pressure values imposed by a device on the airway of the subject the corresponding multiple different times. For each of the ultrasound images, the method also includes automatically forming a mask of pixels associated with an air-tissue interface; and, automatically determining a value of a statistic of pixels within the mask. The method still further includes automatically determining a titration pressure for a continuous positive airway pressure (CPAP) device based on the positive pressures and the value of the statistic for each of the ultrasound images. Even further, the method includes presenting on a display device output data that indicates the titration pressure for the CPAP device.

In some embodiments of the first set, determining the titration pressure includes determining the titration pressure based on one or more of the different positive pressures which occur at one or of the corresponding different times when the value of the statistic of pixels within the mask is above a threshold value.

In some embodiments of the first set, presenting on a display device output data that indicates the titration pressure for the CPAP device includes operating the CPAP device at the titration pressure.

In a second set of embodiments, a method includes automatically receiving first multiple ultrasound images representing a cross sections of an airway in a neck of a subject obtained by an ultrasound transducer array directed toward the subject at corresponding multiple different times. The method also includes determining a region of interest comprising a subset of pixels of each image of the first plurality of ultrasound images, wherein each region of interest encompasses an airway of the subject. The method further includes, for each of the multiple ultrasound images, automatically forming a mask of pixels associated with an air-tissue interface based on both a morphological opening and a morphological closing with a structural element in the region of interest if the mask includes at least a minimum number of pixels. The method still further includes, for each of the multiple images, automatically determining a value of a statistic of pixels within the mask. The method yet further includes presenting on a display device output data that indicates a degree of airway patency proportional to the value of the statistic at each of the corresponding multiple different times.

In other sets of embodiments, a system or a non-transitory computer-readable medium is configured to perform one or more steps of at least one of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings, in which like reference numerals refer to similar elements and in which:

FIG. 5A through FIG. 5C are images from an endoscope and two slices of ultrasound returns, respectively, which illustrate example obstructed airway, according to an embodiment;

FIG. 5D through FIG. 5F are images from an endoscope and two slices of ultrasound returns, respectively, which illustrate example open airway, according to an embodiment;

FIG. 7A through FIG. 7D are block diagrams that illustrate example shape functions that can be used in one or more steps illustrated in FIG. 6A through FIG. 6M, according to various embodiments;

DETAILED DESCRIPTION

Figure 1A:
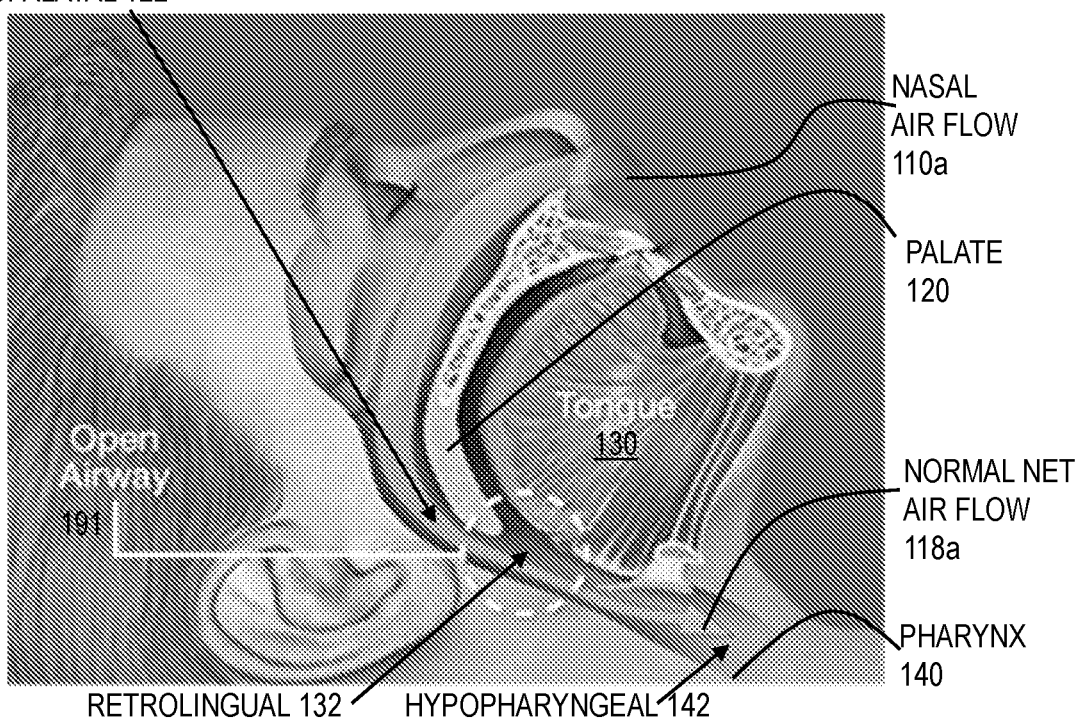
FIG. 1A and FIG. 1B are block diagrams that illustrate example open and obstructed airways, respectively, in a subject.

A method and apparatus are described for the automatic titration of a CPAP device. In some embodiments the techniques automate the localization of an obstruction contributing to obstructive sleep apnea. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5x to 2x, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of ultrasound transducers used in sequence without beamforming to detect reflected energy as a function of time from an airway in a subject. However, the invention is not limited to this context. In other embodiments ultrasound transducers are arrayed to detect transmitted, refracted and scattered energy in addition to or instead of reflected energy from the airway or other tissue structures of the subject, with or without beamforming and with or without computed tomography.

1. REVIEW

Historically, diagnosis of OSA has been achieved through history obtained from the subject and the sleep partner. To increase the sensitivity and specificity of diagnosis, numerous studies have advocated the addition of polysomnographic testing (Riley et al. 1993) that includes a battery of measures including blood oxygenation levels during the apneic episodes, physiological measures such as heart rate, respiratory rate and electroencephalography (EEG). Polysomnography in a certified sleep lab is the gold standard for diagnosis of OSA in current medical care. Other joint task force recommendations (Veasey 2006; Collop 2007) identified a cohort of subjects who could be candidates for portable monitoring (PM) through application of probes and sensors that specifically measure physiological parameters during the episodes of apnea. A large volume of literature has thus evolved, concentrating on the following parameters (Collop 2007): 1. Oximetry; 2. Respiratory monitoring including a) Effort, b) Airflow, c) Snoring, d) End-tidal CO2, e) Esophageal pressure; 3. Cardiac monitoring, not limited to: a) Heart rate or heart rate variability, b) Arterial tonometry; 4. Measures of sleep-wake activity such as a) Electroencephalography, b) Actigraphy; 5. Body position; and 6. Miscellaneous others.

While monitoring technology for these measurements has largely been in place especially during polysomnography (PSG) testing, traditionally called a sleep study, these pave the way only for diagnosis and are specifically deficient for accurate localization of obstructive phenomena. The importance of localization (site of obstruction imaging) is in treatment, wherein an area of obstruction could be surgically ameliorated; or monitored to determine a minimum pressure for continuous positive airway pressure (CPAP), a process called CPAP titration. Thus, diagnosis alone is not sufficient for reducing the progression of the syndrome; does not specifically address the site(s) of obstruction; and, thus does not specifically assist titrating continuous positive airway pressure (CPAP) that works by pneumatically stenting the airway. Furthermore, a technique to monitor and identify the site of obstruction could be a significant milestone in formulating long-lasting treatment strategies for an individual diagnosed with OSA.

The simplest method for assessment of airway geometry involves use of the lateral skull and neck radiographs for cephalometric calculations. A summary of these radiographic findings (Deberry-Borowiecky et al. 1988) in these subjects include (a) enlargement of the tongue and soft palate. (b) inferior displacement of the hyoid bone (c) normal size and position of the mandible, yet changes in the relative positions of landmarks on the mandible itself (d) backward displacement of the maxilla and elongation of the hard palate and (e) normal nasopharynx, but reduction in the oropharyngeal and hypopharyngeal airway diameters. In combination, these findings illustrate the presence of multi-segmental changes within the aerodigestive tract that may be targeted with surgical procedures (Guilleminault et al. 1984; Riley et al. 1985). However, the major disadvantage with these radiographic assessments concerns simultaneity, i.e. obstructive phenomena may occur at multiple levels but the lack of resolution of x-ray findings prevents categorization of obstruction into major and minor phenomena, hence they lose their relevance for accuracy in localization for targeted treatment. Lateral cephalogram radiography also fails to elucidate the importance of soft tissue in the etiology of apnea. A modified technique for obtaining radiographs, i.e. fluoroscopy, wherein live imaging of the airway could be obtained using continuous x-ray exposure has higher sensitivity and specificity (Pepin et al. 1992). However, somno-fluoroscopy is unsuitable for introduction as a screening tool due to exposure to ionizing radiation.

An alternate technique that has been frequently used in literature includes the use of high-resolution CT scans (Bhattacharyya et al. 2000; Rodenstein et al. 1990). Here, the resolution is markedly improved with current technology that permits extremely thin slice acquisitions, and may be combined with a trigger-activated circuitry using pulse oximetry, obtaining scans that may be acquired specifically during the time of obstruction. As promising as it sounds, there are several problems associated with deployment, namely exposure of subjects to high levels of ionizing radiation, loss of natural sleep patterns during acquisition within the scanner bay, and costs. Similar problems exist for use of MRI scanners; even as they increase the resolution of soft tissue imaging (Schwab et al. 2003; Shelton et al. 1993). MRI scanners are noisy, with potential to disrupt sleep; and the time taken for acquisition of images may be prohibitive for large-scale screening; with additional problems associated with motion-artifacts.

One of the earliest studies for localization of OSA obstruction focused on simultaneous monitoring of pressures in the posterior nasopharynx, oropharynx, hypopharynx, and esophagus during overnight polysomnography (Shepard et al. 1990). From the profile of pressures recorded in the upper airway and esophagus, the regions over which the airway collapses during apneic episodes could be determined. While this study yielded the degree of relationship between the pressures and PSG-derived indices, this mandated insertion of monitoring probes invasively within the upper aerodigestive tract and the limitation of the number of subsites indicated that the overall resolution was poor. Others (Chaban et al. 1988) that focused on insertion of catheter-based transducers such as the Millar device also reported benefits in measurement. Conceivable issues with long-term measurements include problems with loss of natural sleep architecture owing to the presence of a device in the upper airway, and safety issues concerning migration and potential for the device itself to cause obstruction. Furthermore, animal models often conclude that there is poor relationship (Hudgel 1986) between pressure gradients measured using deployable transducers and the surgical outcomes following procedures such as uvulopalatopharyngoplasty (UPPP).

In assessments of subjects prior to undergoing sleep surgery, a flexible fiberoptic endoscopic examination of the upper airway has been recommended (Croft et al. 1991) with some confidence owing to the relative ease of this procedure. However, this technique cannot identify subjects who have multisegmental anatomic obstruction (Morrison et al. 1993), and those individuals cannot be accurately tested because the measurements are done in the setting of a clinic in an awake state.

Ultrasound technology has been refined and modified for use in areas such as medical imaging (McNay et al. 1999), non-destructive testing (Silk 1984), industrial processing applications (Ruecroft et al. 2005), cleaning (Muthukumaran et al. 2004), and range finding (Kuratli et al. 2000). Devices used for biomedical applications have been repeatedly appraised and found to be safe (Hoskins et al. 2010) and suitable for use in a variety of settings, such as obstetric (Romero 2003) and fetal (Crane et al. 1994) diagnostic techniques, cardiac and vascular applications including devices such as catheters and probes (Gardin et al. 2006; Hamers et al. 2001).

Ultrasonic devices for use in diagnosis of obstructive sleep apnea have not been thoroughly evaluated thus far; an extensive MEDLINE search for terms "ultrasound" and "obstructive sleep apnea" produced just four relevant results. Two of these articles specifically evaluated ultrasound for prediction of difficult laryngoscopy in obese subjects (Ezri et al. 2003) and for identification of anatomic landmarks prior to procedures such as tracheostomy and cricothyroidotomy (Kajekar et al. 2010). The third, a dissertation (Girard 2003), evaluated a standard ultrasound system to obtain images of the area of the pharynx involved in OSA and utilized image processing algorithms for detection of obstruction. This work also showed that the extracted active contours of the airway accurately detected its state (open or obstructed) in two dimensional axial images of the pharynx. In addition, the author showed that a motion detection algorithm could quantify tongue base movements. Lastly, yet another manuscript (Siegel et al. 2000) evaluated the relationship between ultrasound-derived images and clinical polysomnographic indices, and found good correlation between multiple variables.

2. OVERVIEW

Figure 1B:
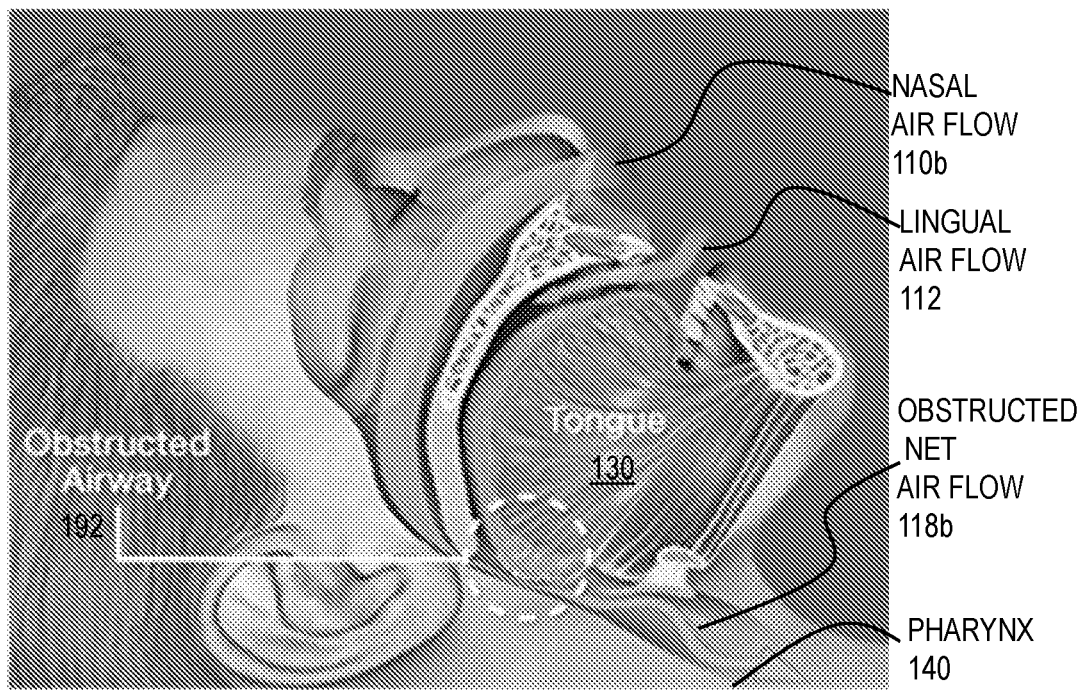

Here is described a method and system that enables one to localize a site of obstruction in subjects with OSA using ultrasound technology and to monitor that site during CPAP titration to determine therapeutic positive pressure for CPAP treatment. To illustrate how the device functions, it is useful to show an example of an airway obstruction in the context of the airway anatomy. FIG. 1A and FIG. 1B are block diagrams that illustrate example open and obstructed airways, respectively, in a subject. The anatomical features of the subject include a soft palate 120, tongue 130 and pharynx 140. An airway is a lumen that includes nasal sinuses inside the nose, a retropalatal portion 122 behind the soft palate 120, a retrolingual portion 132 behind the tongue and a hypopharyngeal portion 142 in front of the pharynx. FIG. 1A depicts normal airflow through the nose (nasal air flow 110a) past the palate 120 and tongue 130 and pharynx resulting in normal net air flow 118a. In particular the airway is open in portion labeled open airway 191. FIG. 1B depicts an obstructed airway 192 in the retrolingual portion of the airway corresponding to open airway 191 in FIG. 1A. This results in obstructed net airflow 118b that leads to mouth breathing indicated by lingual air flow 112, or snoring, or insufficient oxygenation of the subject's blood, or some combination, or worse, leads to essentially zero net flow and risk of death if the subject does not awake in time.

2.1 Structural Overview

Figure 2:
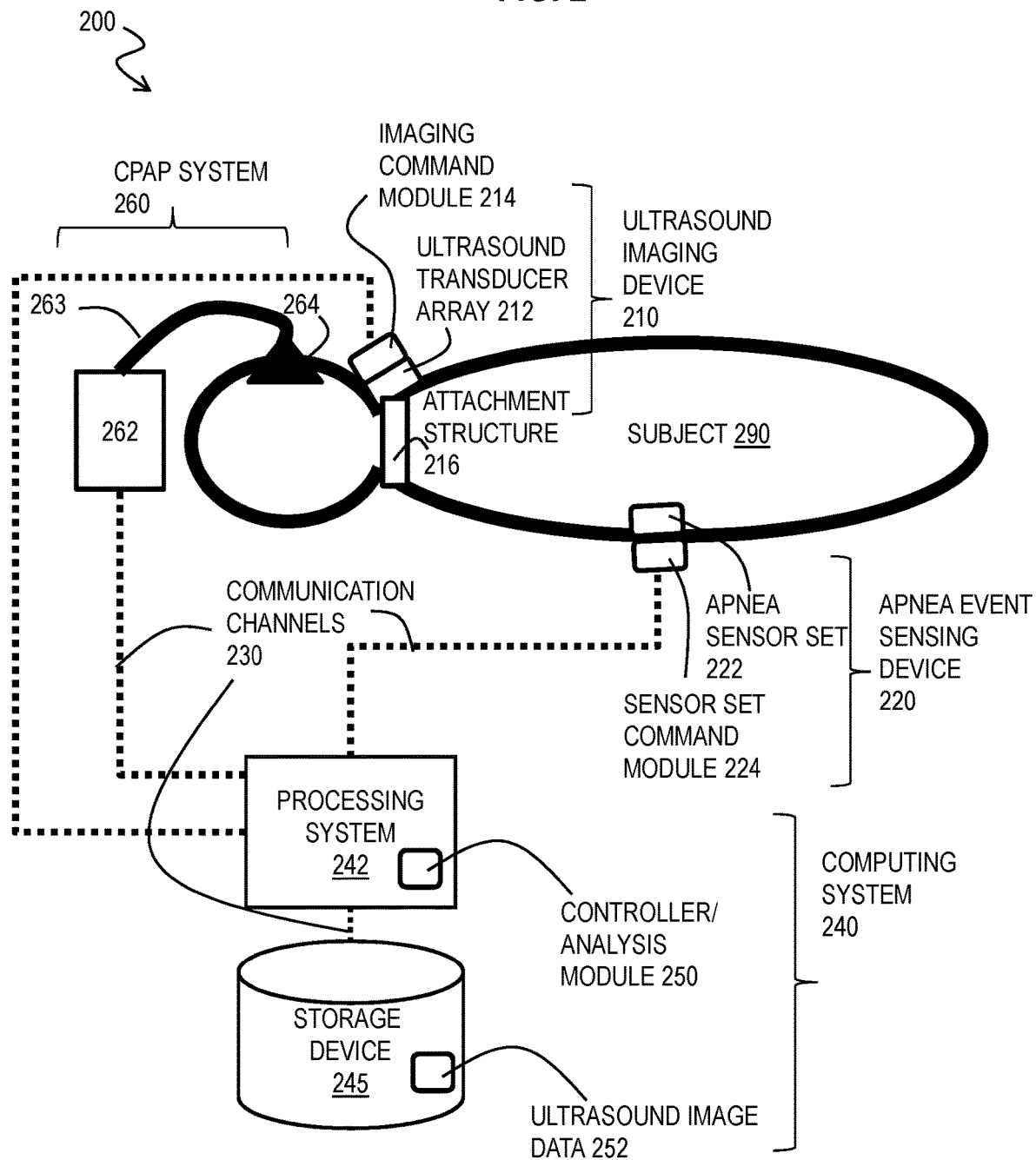
FIG. 2 is a block diagram that illustrates an example system for automatic ultrasound imaging of a subject for determination of location of an obstruction that could contribute to obstructive sleep apnea (OSA) or for automatic CPAP titration, or both, according to an embodiment.

In various embodiments, a system is configured to automatically scan the airway during an obstructive sleep apnea (OSA) event using ultrasound, to provide ultrasound image data that can be used to localize an obstruction, either manually or, in some embodiments, automatically, and to automatically perform CPAP titration based on the localized obstruction, whether the obstruction is localized automatically or manually. FIG. 2 is a block diagram that illustrates an example system 200 for automatic ultrasound imaging of a subject for determination of location of an obstruction that could contribute to obstructive sleep apnea (OSA) or for automatic CPAP titration, or both, according to an embodiment. As used herein, a subject can be any organism with lungs, including animals, mammals and humans, alive or dead. Although a subject 290 is depicted for purposes of illustration, subject 290 is not part of system 200.

The system 200 includes an ultrasound imaging device 210, an apnea event sensing device 220, a CPAP system 260 and a computing system 240, in data communication with each other through one or more data communication channels 230.

The illustrated ultrasound imaging device 210 includes an ultrasound transducer array 212, attached to the subject by an attachment structure 216 such as a strap or belt or collar, and a imaging command module 214. A variety of suitable imaging devices for various embodiments are described in U.S. Patent Application Publication No. US2015/0209001 (hereinafter, Wolf et al., 2015), the entire contents of which are hereby incorporated by reference as if fully set forth herein. If biplane (rotary sagittal plane) ultrasound transducers are of interest, an E14CL4b endocavity biplane (Analogic Corp, Peabody, Mass.); 3DART type 8808 (Brüel & Kjær, Herlev, Denmark) or HD15 BP10-5EC Biplane Curved Array (Philips Healthcare, Andover, Mass.) can be used. An alternate arrangement uses simultaneous biplane scanning with one scanner apiece for each plane, e.g., coronal and sagittal, and subsequent reconstruction by combining sequences using morphological reconstruction. An additional alternate arrangement is configured by combining more than one transducer in each plane. If single-plane, then useful transducers are a C60e transducer (5-2 MHz, Sonosite, Bothell, Wash.), a L12-5 transducer (12-5 MHz, Philips Healthcare, Andover, Mass.), or a L4-12t-RS transducer (12-4 MHz, Wauwatosa, Wis.).

The ultrasound transducer array 212 is a set of two or more ultrasound transducers arranged in one or two dimensions configured to operate together to introduce or detect ultrasound waves. An ultrasound transducer is a component that either produces an ultrasound wave in response to an electrical or optical signal (also called an ultrasound transmitter), or produces an electrical or optical signal in response to an impinging ultrasound wave (also called an ultrasound receiver or detector), or both (also called an ultrasound transceiver). In various embodiments, ultrasound transducers are arrayed to detect transmitted, reflected, refracted or scattered energy from the airway or other tissue structures of the subject, with or without beamforming, and with or without computed tomography. Many ultrasound transducers appropriate for probing human tissues are known in the art and any may be used in various embodiments. Example ultrasound transducers are described below. The ultrasound transducer array 212 is configured to produce data for multiple ultrasound images representing corresponding multiple cross sections of an airway of the subject 290 at multiple different times, as described in more detail below.

The imaging command module 214 is a component that powers and activates the transducer array and transmits data representing the received signals that are used to construct an image. In some embodiments, the command module also constructs the image data based on the received signals. Many ultrasound probes are commercially available with a command module and transducer array as an integrated unit. Examples of such integrated ultrasound probes include: icte and c60e from SONOSITE™ of Bothell, Wash.; 8820e from ANALOGIC™ Corporation, Peabody, Mass.; 10C-D, 10C-SC, 3S-SC, RAB series from GE HEALTHCARE™, Little Chalfont, Buckinghamshire, United Kingdom; EUP-C715, C514, C516, C511, C524 and C532 (convex probes) from HITACHI ALOKA™ Medical America, Wallingford, Conn.; SP2730, CA1123, LA533, LA523 from ESAOTE™ North America, Inc. Indianapolis, Ind.

The CPAP system 260 includes an electrically controlled pump 262 connected by air hose 263 to face mask 264 configured to fit over the nose and mouth of the subject 290. In some embodiments, the system 260 includes one or more sensors configured to detect the air pressure and zero or more other properties, such as temperature, of the volume of air inside the face mask and mouth and nose of the subject 290. Signals representing commands for the pump, such as a pumping rate or target pressure are supplied by the processing system 242 through one or more communication channels 230. In some embodiments, data indicating the most recent command or a series of commands is stored locally on the pump. Signals representing the detected pressure and zero or more other properties are transmitted through one or more of the communication channels 230 to the pump 262 or processing system 242, or some combination. Example CPAP systems include Transcend Auto MINICPAP™ Machine (Somnetics, New Brighton, Minn.); AIRSENSE™ 10 AutoSet (ResMed, San Diego, Calif.); PR System One REMStar 60 Series (Philips Respironics, Murrysville, Pa.); XT Fit CPAP Machine (Apex Medical, New Taipei City, Taiwan); Icon Auto CPAP (Fisher & Paykel, Auckland, NZ).

The computer system 240 is one or more devices, such as a computer system 2000 described in more detail below with reference to FIG. 20, or a chip set, such as chip set 2100 described in more detail below with reference to FIG. 21 and used for example in a portable or mobile device such as a cell phone or tablet. The computer system is configured to control the operation of the ultrasound imaging device 210, and to produce, present or store all or part of the ultrasound image data, or some combination. Many commercially available ultrasound probes are available with terminal equipment that performs some or all of the functions of the computing system 240. Examples of such ultrasound imaging terminals include point of care stations for one or more of the above probes and MyLab Twice, MyLab Seven, MyLab Gold from ESAOTE™ North America, Inc. Indianapolis, Ind.; and, Voluson E10, E8 and E6, Vivid E9, S6, q, S5 LOGIQ e Ultrasound BT 12 from GE HEALTHCARE™, Little Chalfont, Buckinghamshire, United Kingdom.

The computing system 240 is also configured to control the operation of the CPAP system. Example CPAP systems that can be controlled by externally provided digital or analog commands include iVent 201 from VersaMed, Pearl River, N.Y. and Stellar 150 from ResMed, San Diego, Calif.

According to the illustrated embodiment, the computing system 240 includes at least a processing system 242 and storage device 245. The processing system 242 includes hardware and software configured to perform the steps of a novel controller/analysis module 250, as described in more detail below with reference to flow charts in FIG. 12 and FIG. 13. At least some image data that indicates location of an obstruction during an obstructive sleep apnea (OSA) event is stored as ultrasound image data 252 on storage device 245, which is one form of computer-readable memory, as described in more detail below with reference to FIG. 14 and FIG. 15.

Rather than have the ultrasound imaging device 210 and computing system 240 perform the computationally, algorithmically and power demanding task of constantly imaging the tissues and airways of the subject to determine the timing of an OSA event, in some embodiments, The system determines the timing of an OSA event based on a separate apnea event sensing device 220. The device 220 includes an apneas sensor set 222 of one or more sensors that collect measurements that are sensitive to the occurrence of an OSA event, such as interruption of normal chest movement rhythms, a drop in blood oxygen saturation levels, or the interruption of normal acoustic rhythms such as the sounds of breathing or snoring. Sensors typically used for such purposes include microphones to detect the audible sounds made by the subject, blood oxygen saturation sensors such as a pulse oximeter attached to a subject's finger, and one or more accelerometers attached to a subject's chest. The absence of airflow (sensor output) during sleep (EEG) while the chest is moving with resultant decreased saturation (desat) is how a sleep lab would diagnose and OSA event. Example sensors include Airflow sensors, Pulse Oximeter, chest movement sensors, and EEG (to detect sleep), such as SOMNOSTAR™ v4 from VIASYS™ Inc of Conshohocken, Pa.; and, e-series and SOMTEPS™ from COMPUMEDICS™, Victoria, Australia. Such sensors are simpler, more rapid or more cost effective than the ultrasound imaging device 210, or offer some combination of these advantages. In some embodiments, it is advantageous to use at least two such sensors, of the same or different types or some combination, to provide reliability and redundancy as a safeguard against failure of a single sensor.

In the illustrated embodiment, the apnea event sensing device 220 includes a sensor set command module 224 to power or control the sensors in the sensor set 222, ensure the sensors are functioning properly, or send an alarm when the sensor data indicates an OSA event, or some combination. In embodiments involving CPAP titration, the titration process itself may prevent the occurrence of a sleep apnea event; and, in some such CPAP titration only embodiments, the apnea event sensing device 220 is omitted.

The data communication channels 230 are wired or wireless channels (including BLUETOOTH and WiFi) in direct or networked communication within, between or among two or more of the ultrasound imaging device 210, CPAP system 260, apnea event sensing device 220 and computing system 240. One or more of the devices 210, 220, 240, 260 is configured to establish communications within or among the devices, for example using standard networking protocols.

The system 200 is configured such that, when an OSA event is detected based on data from the advantageous sensors of the apnea sensor set 222, a signal is sent to the ultrasound transducer array 212 to collect imaging data for forming images of the airway of the subject at multiple cross-sections of the airway, from the retropalatal region down past the hypopharyngeal region. Thus, data is collected that can indicate the location of an obstruction. In some embodiments, a human analyst reviews the images to determine the occurrence of any obstruction. In some embodiments, the system automatically identifies one or more of the images, or regions within the images, or some combination, with features likely to indicate the location of an obstruction.

After the obstruction location is determined, either automatically or manually, that location is monitored using multiple subsequent ultrasound images collected at corresponding multiple different times while increasing pressures are exerted by the CPAP system in a CPAP titration process. That process automatically terminates when the pressure applied is sufficient to maintain or re-open an open airway without being unduly uncomfortable to the subject. For example, in some embodiments, the pressure increase is mapped to the number of sleep apnea events, and the titration pressure is reached when the count drops below a certain level, e.g., 1 event per night. In other embodiments, the pressure is not applied until a sleep apnea event is detected, then a slowly increasing pressure is applied to re-open the airway. Each pressure increment is coordinated with an ultrasound image through the obstruction location. The pressure that re-opens the airway is considered a potential CPAP pressure. Because the pressure to re-open an airway might be greater than the pressure sufficient to prevent closing of the airway, in some embodiments, the potential CPAP pressure is reduced slightly and maintained to obtain a count of sleep apnea events at the slightly reduce pressure. The process is repeated until a pressure is found that separates an unacceptably high count of sleep apnea events (e.g., more than X event per 8 hours of sleep, where X varies from about 1 to bout 5) from an acceptable count of sleep apnea events (e.g., X events or fewer than X events per eight hours of sleep). In some embodiments, a strength of the air-tissue interface is know to be associated with unobstructed sleep, and the pressure is increased until that strength is achieved without waiting for a sleep apnea event to occur which is expected to be rare.

Although processes, equipment, and data structures are depicted in FIG. 2 as integral blocks in a particular arrangement for purposes of illustration, in other embodiments one or more components or processes or data structures, or portions thereof, are arranged in a different manner, on the same or different equipment, in one or more databases, or are omitted, or one or more different components or processes or data structures are included on the same or different equipment. For example, processing done by the imaging command module 214 or the sensor set command module 224, or both, may be performed in whole or in part by the controller/analysis module 250 in the computer system 240. Likewise, some or all functions performed by the controller/ analysis module may be performed by the imaging command module 214 or sensor set command module 224, or some combination.

Thus, the system 200 includes an ultrasound transducer array 212 configured to be disposed adjacent to a neck of a subject, a continuous positive airway pressure (CPAP) device 260, at least one processor 242; and at least one computer-readable medium 245. The computer-readable medium include one or more sequences of instructions, such that the at least one medium and the one or more sequences of instructions are configured to, with the at least one processor, cause the system to perform at least the following steps. The system automatically receives multiple ultrasound images representing a cross section of an airway in a neck of the subject obtained by the ultrasound transducer array directed toward the subject at corresponding multiple different times. The system automatically receives data indicating multiple different positive pressure values imposed by the CPAP device on the airway of the subject at the corresponding multiple different times. For each of the multiple ultrasound images, the system automatically forms a mask of pixels associated with an air-tissue interface, and automatically determines a value of a statistic of pixels within the mask. The system also automatically determines a titration pressure for the CPAP device based on the multiple positive pressures and the value of the statistic for each of the multiple ultrasound images. In addition, the system operates the CPAP device at the titration pressure.

Figure 3:
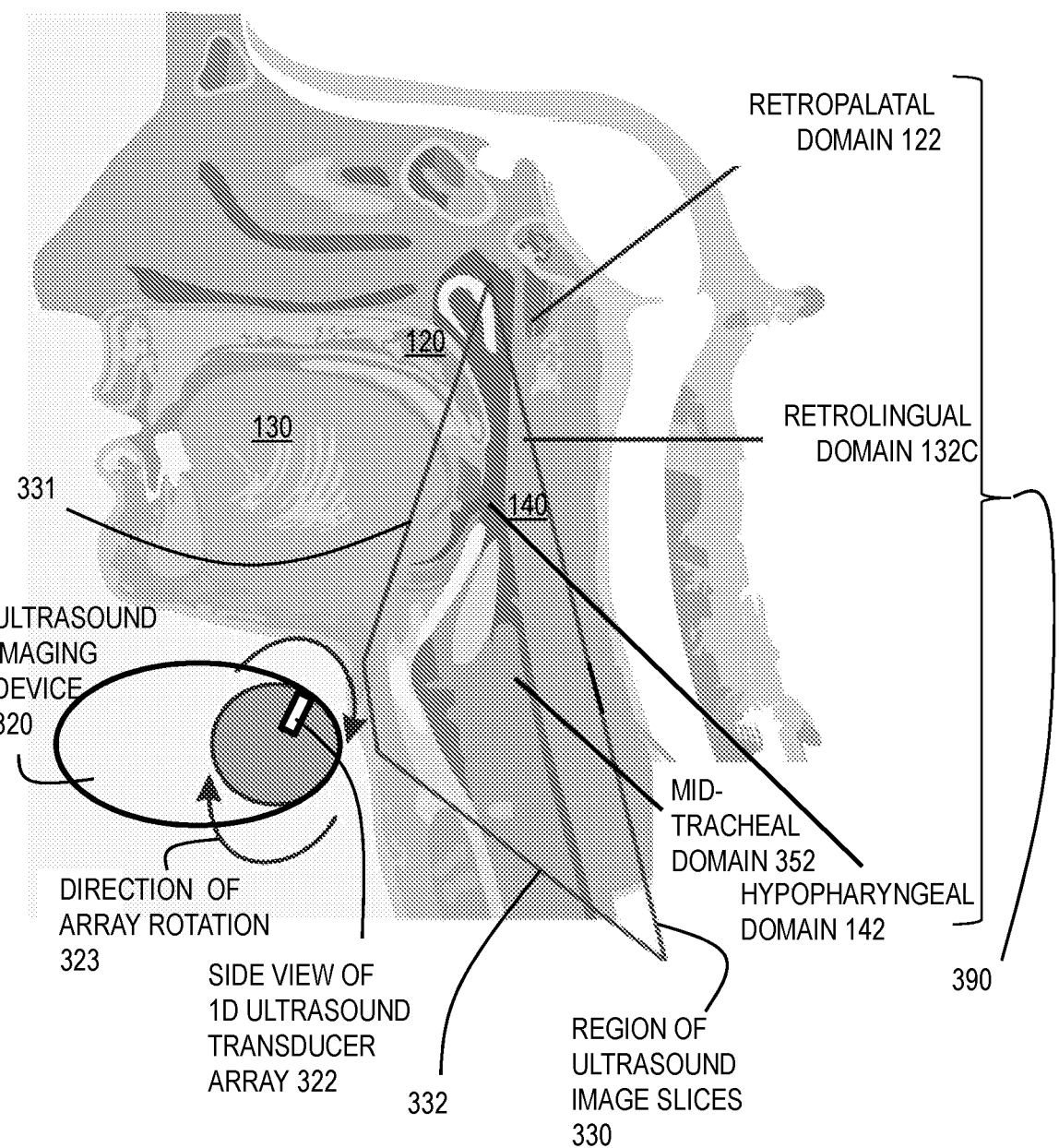
FIG. 3 is a block diagram that illustrates an example rotating 1D array of ultrasound transducers used to acquire multiple 2D ultrasound images, as used according to some embodiments.

FIG. 3 is a block diagram that illustrates an example rotating 1D array 322 of ultrasound transducers used to acquire multiple 2D ultrasound images, as used according to some embodiments. The array 322 is depicted in side view looking along the axis of rotation so that the angular rotation is in direction 323. The rotating 1D array 322 is housed in an ultrasound imaging device 320, which can be held in place to simulate a device strapped to the throat of the subject 390. Although depicted for purposes of illustration, the subject 390 is not part of the device 320.

In one orientation, the 1D array 322 produces a 2D image along a cross section perpendicular to the view of FIG. 3 along a top side 331 of trapezoidal region 330. In a different orientation, the 1D array 322 produces a 2D image along a cross section perpendicular to the view of FIG. 3 along a bottom side 332 of trapezoidal region 330. In between these two images, multiple 2D images are produced along intervening cross sections. Note that the cross sections are not parallel in this embodiment, but yet sample the airway from the retropalatal domain 122, through the retrolingual domain 132 and the hypopharyngeal domain 142 to the mid-tracheal domain 352.

To study the automated identification of an ROI encompassing an obstruction, the ultrasound imaging device 320 was used in an experimental embodiment in which the subject was a cadaver. The cadaver was surgically altered to allow tissue collapse to be induced. Soft tissue collapse was induced by application of sustained negative pressure (−5 cm of water) via a reversed tracheostomy tube. This negative pressure just exceeds the mean critical pharyngeal closing pressures in humans.

Figure 4:
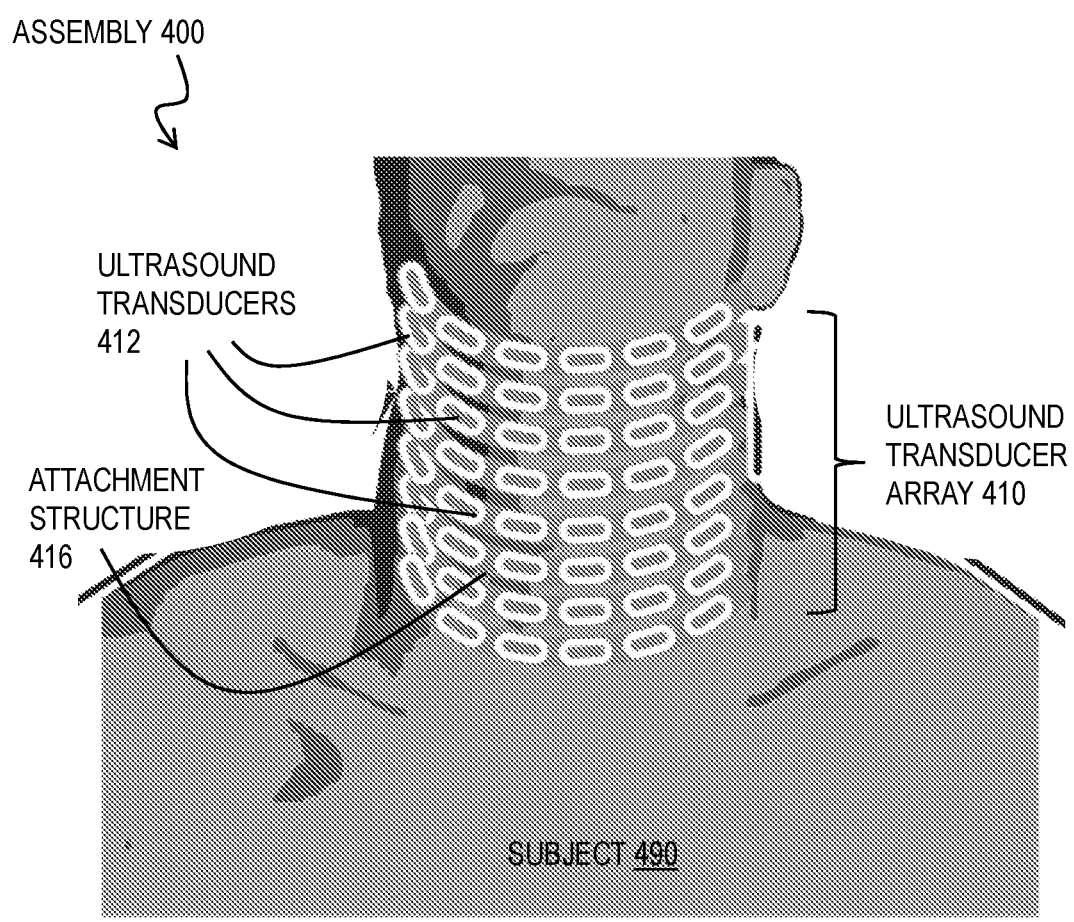
FIG. 4 is a block diagram that illustrates an example curved two dimensional array that follows a curvature of an attachment structure when the attachment structure is removably fitted around a neck of the subject, according to some embodiments.

FIG. 4 is a block diagram that illustrates an example curved two dimensional array 410 that follows a curvature of an attachment structure 416 when the attachment structure is removably fitted around a neck of the subject, according to some embodiments. The individual ultrasound transducers 412 are affixed to the removable attachment structure 416. Thus, FIG. 4 illustrates a circumferential scanner assembly 400 that holds the transducers. In some embodiments, the assembly 400 is held within an expandable, elasticated and tubular fabric (e.g. Dacron) with radial and linear reinforcements as attachment structure 416. These reinforcements prevent the proximal-to-distal and lateral migration of the assembly 400.

FIG. 5A through FIG. 5C are images from an endoscope and two slices of ultrasound returns, respectively, which illustrate example obstructed airway, according to an embodiment. FIG. 5D through FIG. 5F are images from an endoscope and two slices of ultrasound returns, respectively, which illustrate example open airway, according to an embodiment. The airway in the cadaver model is nearly closed as depicted in FIG. 5A so that the endoscope can not penetrate further to actually image the obstruction, while the airway is open much wider in FIG. 5D. The ultrasound images are bright where a strong acoustic reflection is measured and dark where there is little and black where there is none. The airway would be in the posterior 40%, indicated by the horizontal arrow 502 and vertical arrow 504, because in this experiment the acoustic source is at the throat as depicted in FIG. 3 at the bottom of the images. The posterior 40% of the ultrasound images show very low signal. Yet this is the area where an open airway would present an air-tissue interface and a strong reflection signal. The rectangles indicate a small reflection attributed to a pocket of air in the cross section and were placed manually. These small areas of bright pixels are compatible with the significantly diminished air column observed and depicted in FIG. 5A. In contrast, when the airway in the cadaver model is open as depicted in FIG. 5D, the ultrasound images depicted in FIG. 5E and FIG. 5F are bright where an open airway presents an air-tissue interface and a strong reflection signal in the back third of the image. The bright areas attributed to the open airway are marked by a bright outline that has been imposed manually on the image. As can be seen, the number of bright pixels is related to the degree of opening of the airway. A challenge is to detect the bright airway pixels automatically.

In various embodiments, ultrasound cross-sectional images of the airway are automatically processed to determine the area of high reflection attributable to the tissue-airway interface. In some of these embodiments, the manual outlines are used to define manually-determined masks that establish the presence of an air-tissue interface. These correspond to wherein an air column is present. The mask is confined to the top 40% of the neck (posterior in transducer orientation) as the air-tissue interface is always found in the same location. Spatial restriction of the mask reduces contamination from artifacts.

FIG. 6A through FIG. 6M are images that illustrate automated processing steps applied to the image of FIG. 5F in order to find in an ultrasound image pixels associated with an air tissue interface that can be used for automated quantification of patency and possibly detection of obstructions or automated CPAP titration, or some combination, according to various embodiments.

Figure 6A:
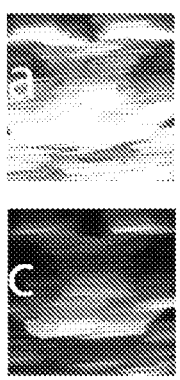
FIG. 6A through FIG. 6M are images that illustrate automated processing steps applied to image of FIG. 5F in order to find in an ultrasound image pixels associated with an air tissue interface that can be used for automated quantification of patency and possibly detection of obstructions or automated CPAP titration, or some combination, according to various embodiments.

The representative image of FIG. 5F with a prominent air-tissue interface is first dilated using a diamond-shaped structuring element that is convolved with the original image, producing the image of FIG. 6A, reduced in scsle to allow multiple such processed images to be presented in the figures. The diamond shaped structural element is depicted in FIG. 7A. In other embodiments, other shapes of dilation structural elements are used. FIG. 7A through FIG. 7D are block diagrams that illustrate example shape functions that can be used in one or more steps illustrated in FIG. 6A through FIG. 6M, according to various embodiments. A value of 1 is inside the element and a value of zero is outside the element for a window of 7 pixels by 7 pixels containing the diamond structural element. During the dilation, the structural element is centered on a pixel in the original image, and the original value at that pixel is multiplied by the value of the structural element and placed in the corresponding position in the processed image relative to the original pixel at the center of the structural element. Alternative shapes are compared to the diamond values. The target shapes are outlined by broken lines and represent the pixels of interest to be convolved with a value of 1, and the pixels outside (neighborhood) represent other pixels convolved with a value of 0 (only the diamond values are actually shown for comparison). FIG. 7B shows a hexagonal outline; FIG. 7C shows a circular outline; and, FIG. 7D shows a rectangular outline. The size and shape of the structuring element may be set manually, following inspection of the air-tissue interface in an initial scan of the neck soft tissues. Other shapes and sizes may be drawn in a custom fashion, should the target airway interface not be accurately modeled by any of the above structural element shapes. The diamond-shaped structuring element was chosen to approximate the contact surface of a transducer (rectangle) making tangential contact with a cylinder (approximating the shape of the neck). It is reasonable to expect a rectangular structuring element would be advantageous for an interface that is perpendicular to the ultrasound transducer, but in practice the best structuring element shape is determined by experiments and is expected to be based on the patient's anatomy.

Figure 6B:
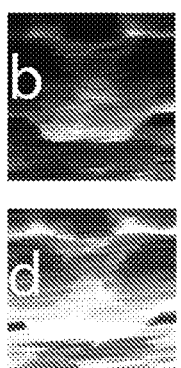

The dilation results in enlargement of the boundaries of regions deemed to contain bright pixels within the foreground, as depicted in FIG. 6A. It is possible to change the sensitivity and specificity of detection by providing an option to change the threshold for what is considered bright, e.g. 150 grey level units. Foreground on the other hand could include all non-zero values within the image. The converse occurs following erosion, which partially removes the interfaces of bright foreground pixels, as depicted in FIG. 6B for the same original image presented at the same scale. Morphological opening results in preservation of foreground regions that have a similar shape to the original structuring element, while eliminating all other regions of foreground pixels. The result of morphological opening is depicted in FIG. 6D for the same original image at the same scale. Closing results in preservation of the dark pixels (ascribed to a "background region") that have a similar shape to the structuring element is shown in FIG. 6C. Although any of these morphological operations may be used to reconstruct the air-tissue interface, the best results are obtained in this instance with an eroded image (also called a "marker" image) that is operated on by morphological opening utilizing the original image. In this reconstruction, the eroded image of FIG. 6B is repeatedly dilated until its contours fit the manual mask generated from the original image. This result is shown in FIG. 6E, at a larger scale.

Figure 6F:
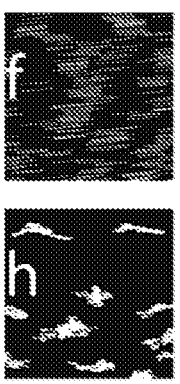

Using the latter approach, the original image was first eroded followed by dilation (morphological opening) to produce FIG. 6F, presented at the smaller scale, again, for convenience. Following this, the regional maxima were estimated. Regional maxima are connected edges of pixels with a constant intensity value, and whose external boundary pixels are lower. The estimation method uses 8-connected neighborhoods in this example, but may be increased or decreased neighborhoods in other embodiments to optimize detection.

Figure 6G:
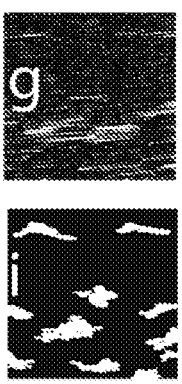
Figure 6K:
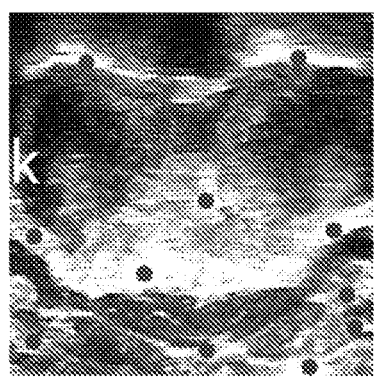
Figures 6C, 6D:
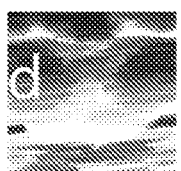
Figure 6H:

In an alternative approach, the original image undergoes dilation first and then erosion producing the image of FIG. 6G, presented at the smaller scale. Regional maxima were also estimated in a similar fashion.

Figure 6I:
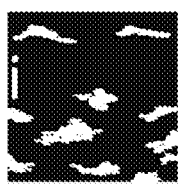
Figure 6E:
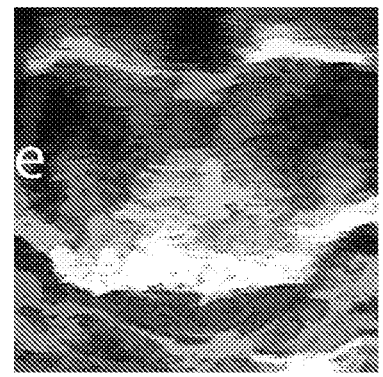
Figure 6J:
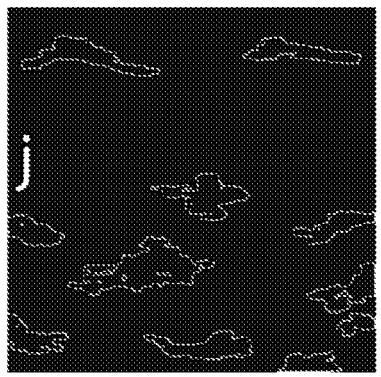
Figure 6L:
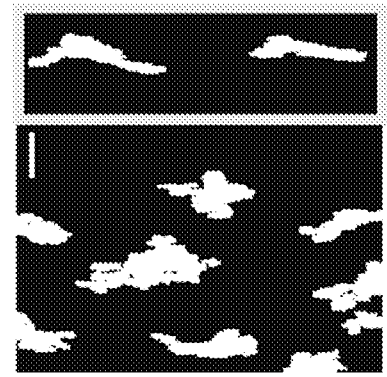

The regional maxima of FIG. 6E were also obtained and shown in FIG. 6H, again at the smaller scale. The image of FIG. 6I represents the effect of removing small objects, deemed to contain fewer than 20 pixels, from the image of FIG. 6H. The definition of small objects to be removed may be increased or decreased as desired in various embodiments. FIG. 6J presents at the larger scale, the outlines of the regional maxima depicted in FIG. 6I. These outlines, when filled with the value 1 inside and the value 0 outside, serve as a mask that can be used to determine the statistics of pixels in the air-tissue interface. The maximum value inside these outlines (within the mask) on the original image produce the spots plotted in FIG. 6K over the original image. Mean pixel intensity was calculated within the marked regions in the posterior 40% and compared to manual estimations. In FIG. 6L, presented at the larger scale, the bright pixels of the mask of FIG. 6I within the box demarking the posterior 40% represent air-tissue interfaces corresponding to an air column and used to calculate area of the air-issue interfaces. In other embodiments, other statistics of the bright pixels can be used, such as the average intensity in the original image within a mask formed by the bright areas of FIG. 6L in the posterior 40%, or median ($50^{th}$ percentile) or the $75^{th}$ percentile or other percentile intensity value inside the mask among others.

Figure 6M:
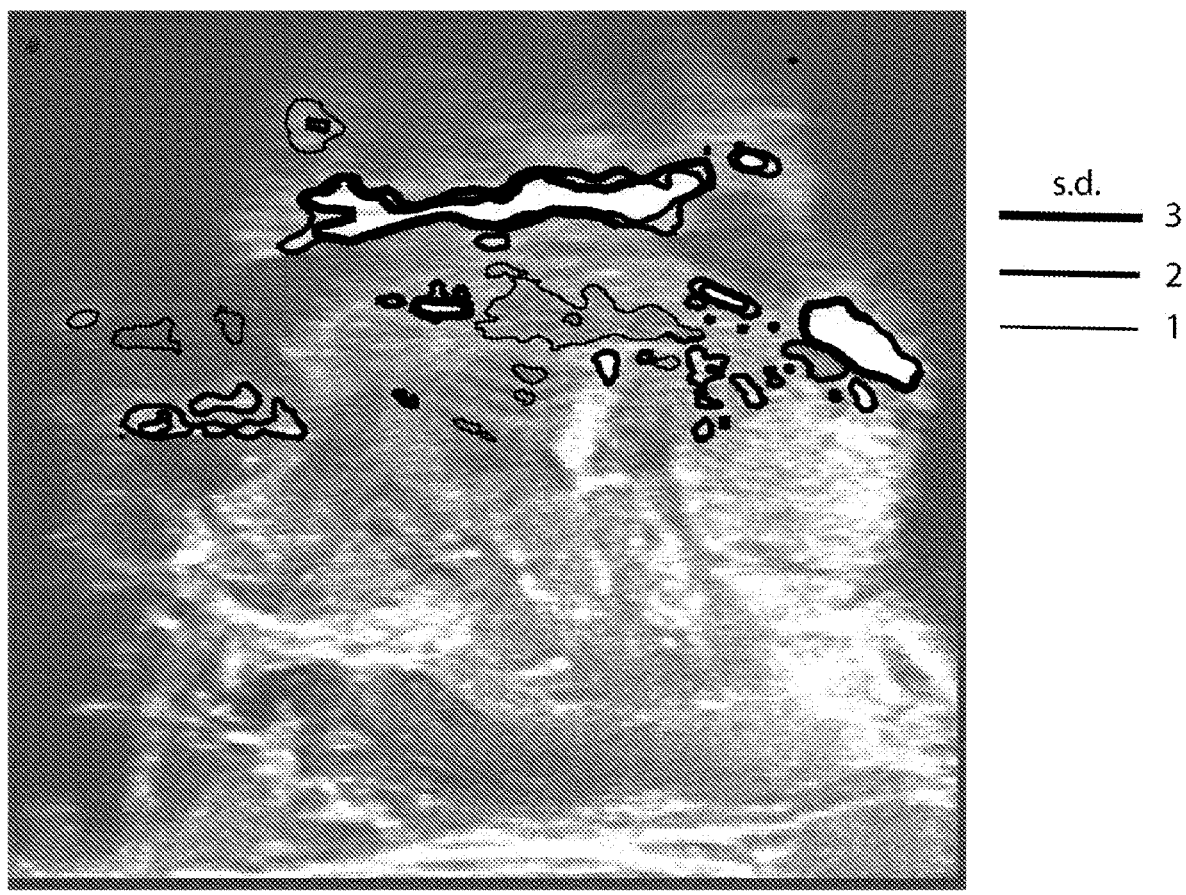

For example, in some embodiments, the posterior 40% (alternatively, 50%) of each image is selected automatically for further processing. A median filter is applied automatically to remove the noise within the selected portion of the image. A Gaussian curve is fit automatically over the distribution of pixel intensities in the selected portion. The Gaussian curve is automatically split into a predetermined number n of bins, with n predetermined to be in a range from about 3 to about 5. In some embodiments, the bin size is determined automatically to be one standard deviation from the Gaussian curve fit step. The bins to the right of the median are examined automatically to determine which bin boundary will serve as the bright interface (mask boundary). The result is illustrated in FIG. 6M, which is an example ultrasound image of the upper airway, axial section. One contour represents the far right bin (above 3 standard deviations) of the Gaussian fitted to pixel intensities within the top half of the image. Note that the contour wraps around the edges of the pixels having intensities in the selected bin. Other contours represent other bin boundaries at 2 standard deviations and 1 standard deviation, respectively, serving as the bright interface (mask boundary) in other embodiments.

Figure 8A:
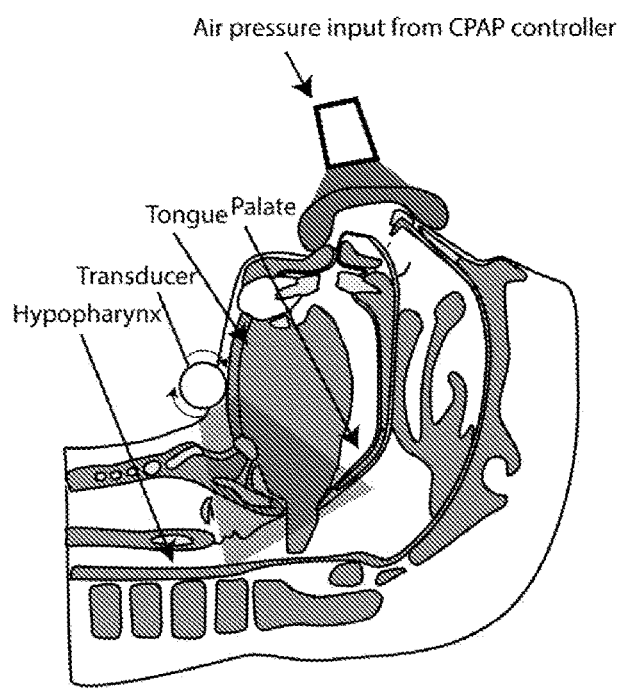
FIG. 8A and FIG. 8B are block diagrams that illustrate example response of an airway to an increase in CPAP pressure, according to various embodiments.
Figure 8B:
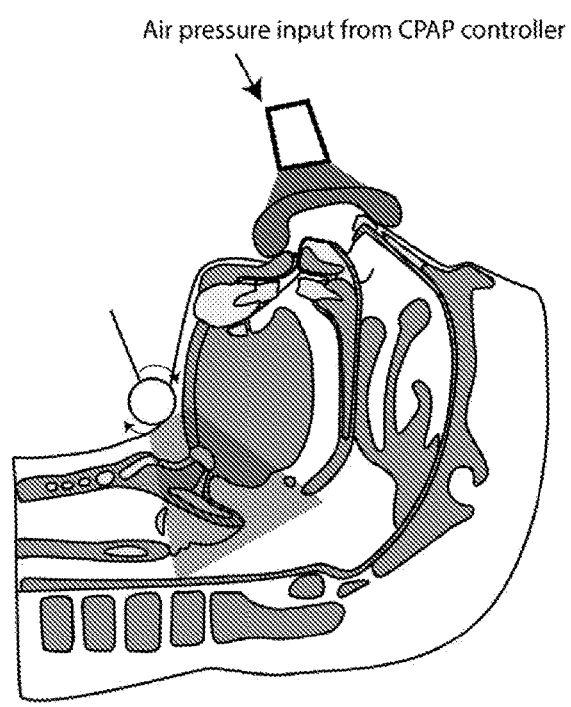

FIG. 8A and FIG. 8B are block diagrams that illustrate example response of an airway to an increase in CPAP pressure, according to various embodiments. Major potential sites of upper airway obstruction are labeled (tongue, palate and hypopharynx). A fitted mask attached to the CPAP machine is also shown. Insufflation pressures are derived by a CPAP control unit. The imaging extent of the ultrasound transducer (5 MHz center frequency) is demonstrated by a greyed-out zone. In FIG. 8A the airway is obstructed by the posterior portion of the tongue in the retrolingual region. FIG. 8B shows upper airway obstruction relieved by adjustments in pneumatic pressure delivered by the CPAP machine. This effect should be noticed in ultrasound cross sectional images that illuminate the retrolingual region.

Figure 9:
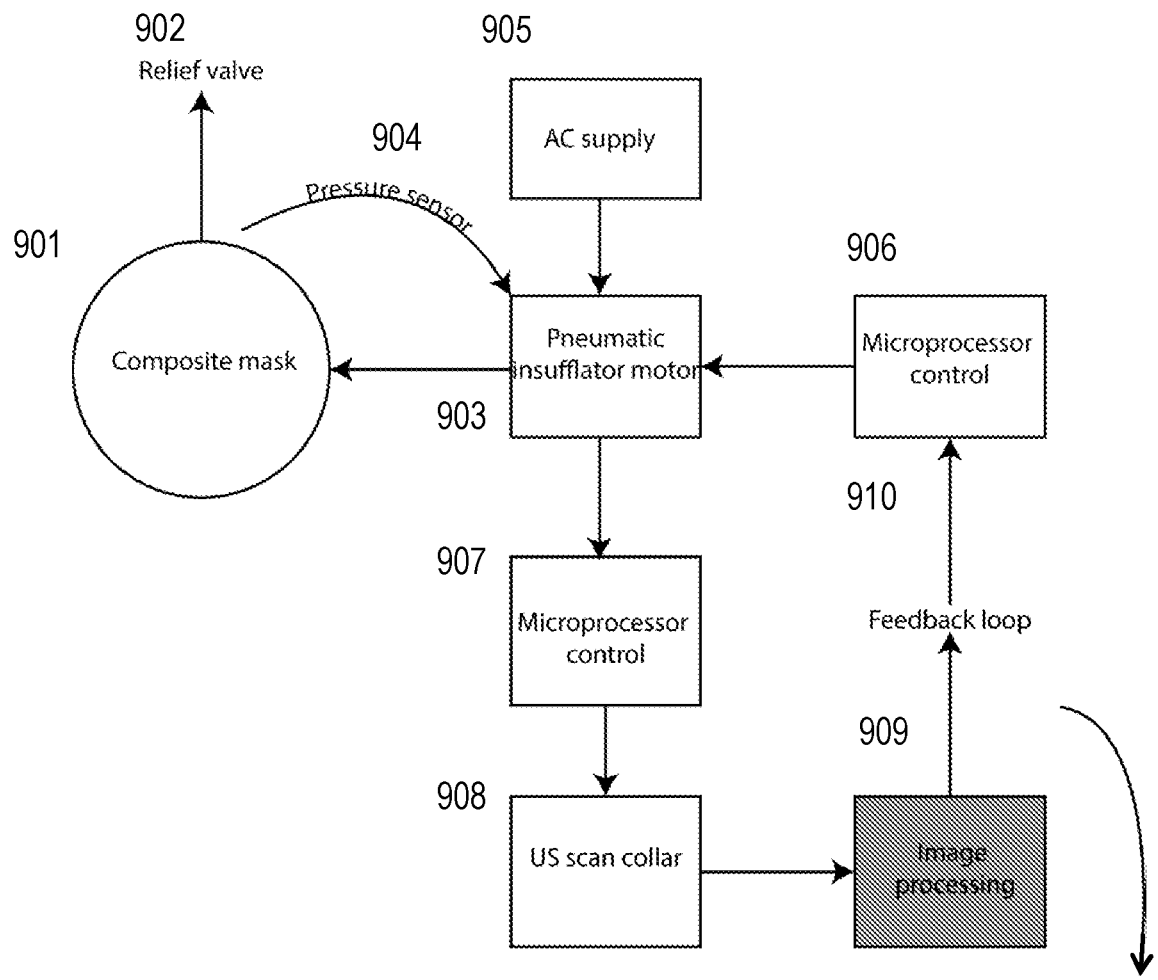
FIG. 9 is a block diagram that illustrates a feedback loop for in an apparatus arranged to perform automated CPAP titration, according to an embodiment.

FIG. 9 is a block diagram that illustrates a feedback loop for in an apparatus arranged to perform automated CPAP titration, according to an embodiment. Application of pressure to the upper airway is by means of a composite mask 901 fitted to the lower face, covering the mouth and the nose, with an attached relief valve 902 to protect against over-inflation. A pneumatic pump (e.g., insufflator motor 903) drives the insufflation of the airway by delivery via the mask 901. The insufflation feedback is controlled using information from an attached barometric sensor 904. These components are all powered by an external, but isolated and grounded power supply 905. The master control mechanisms are modules configured on one or more microprocessors (e.g., 906 and 907) that are in communication with the ultrasound scanner, such as scan collar 908, which provides an estimate of airway obstruction using one or more of the microprocessors 906 and 907 to perform image processing as described above based on overall measurement of airway-tissue interface pixel intensities. One or more microprocessors 906 and 907, cycle the pressure used to insufflate the CPAP mask, forming one or more feedback loops 909 and 910.

Figure 10:
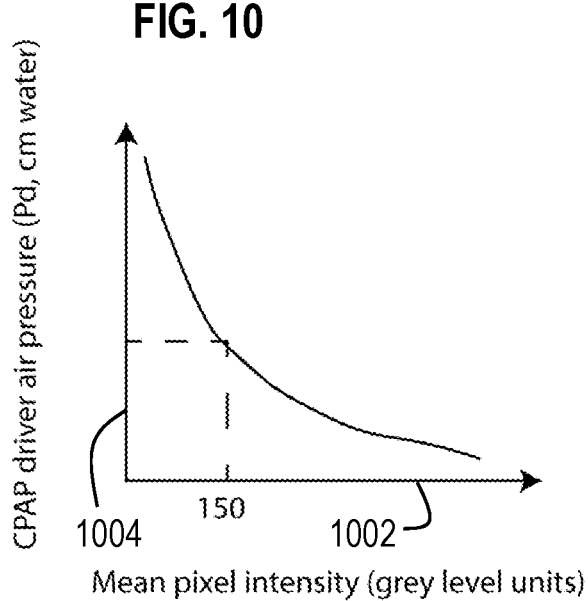
FIG. 10 is a graph that illustrates an example relation between automatically determined pixel intensity at a tissue airway interface and CPAP pressure, according to an embodiment.

This amount of pressure to apply calculated in the feedback loop is explained graphically, with an inverse relationship between CPAP driver pressure (Pd, in cm of water, y-axis) and the normalized pixel intensity (x-axis) of the region of interest determined in an automated fashion using the image processing protocol described above. FIG. 10 is a graph that illustrates an example relation between automatically determined pixel intensity at a tissue airway interface and CPAP pressure, according to an embodiment. The horizontal axis 1002 indicates mean pixel intensity in units of grey level. In other embodiments, the horizontal axis is number of bright pixels in the mask of FIG. 6L. The vertical axis 1004 indicates CPAP driver pressure (Pd) in units of centimeters of water. An example threshold of 150 grey level units is achieved at a re-opening pressure (that matches the closing pressure of the upper airway). Thus this pressure associated with 150 grey level units is the titrated pressure discovered. The CPAP is operated at this insufflation pressure to prevent barotrauma. This threshold can be adjusted according to subject comfort, e.g., reduced somewhat as long as the bright pixel count or mean pixel intensity within the mask does not fall too far below the threshold levels. Some embodiments use a dial or other control to select a value in the range from about 100 to about 150 grey level units for mean intensity and then use a second dial or other control to select a number of standard deviations above that within the mask, e.g. 1 to standard deviations in intervals of about 0.5 standard.

Figure 11:
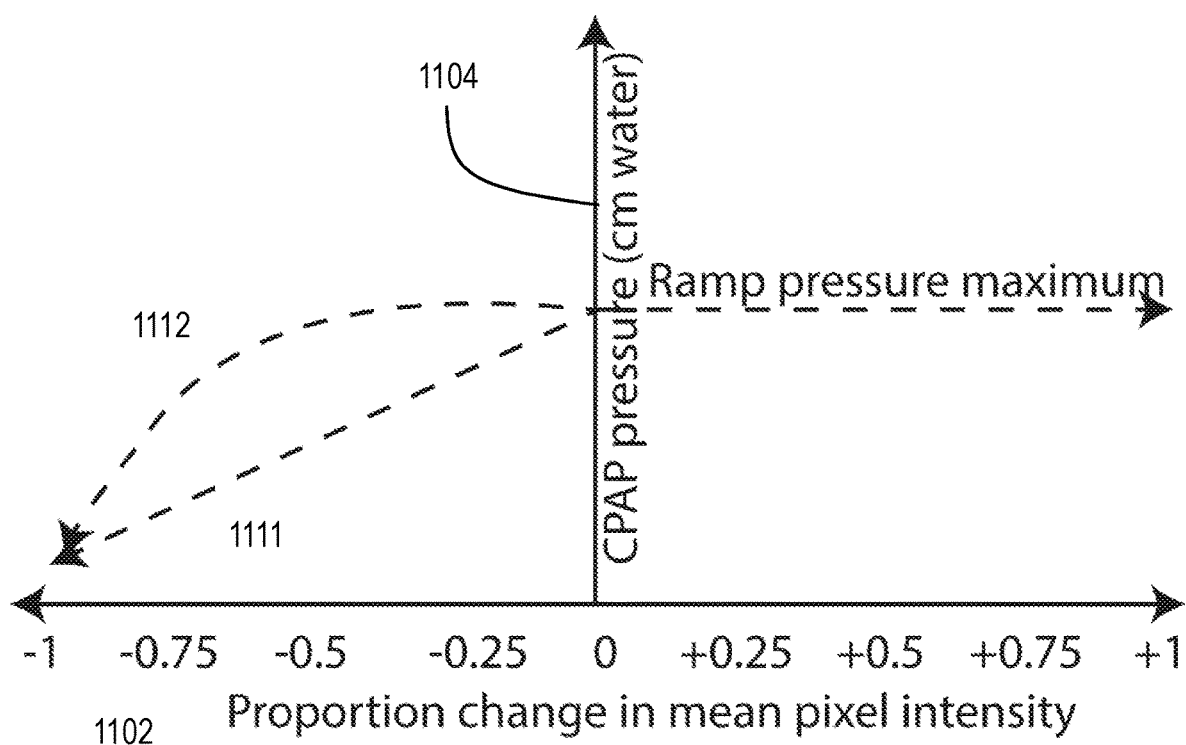
FIG. 11 is a graph that illustrates an example relation between automatically determined pixel intensity at a tissue airway interface and automatic change in CPAP titration pressure, according to an embodiment.

FIG. 11 is a graph that illustrates an example relation between automatically determined pixel intensity at a tissue airway interface and automatic change in CPAP titration pressure, according to an embodiment. The horizontal axis 1102 indicates proportion change in mean pixel intensity and the vertical axis 1104 indicates CPAP pressure in cm H2O. Example functions 1111 and 1112 are shown for titrating CPAP pressures from fitting to measurements of the airway degree of openness from the ultrasound images (called ultrasonographic estimation of airway patency), as measured by bright pixel count or mean pixel intensity within the mask. Functions marked 1111 and 1112 (linear and exponential) model the measured relationship between insufflation pressure using CPAP (y-axis) and the proportion change in mean pixel intensity (x-axis). The mean pixel intensity may be titrated to a desired 'set-point' represented by zero on the horizontal axis 1102, according to subject comfort. Once this set point is reached, the CPAP pressure can be reduced. Other functions that may be biologically appropriate include the Cantor function, characterized by linear non-monotonic growth observed between pixel intensity and CPAP driver pressure, with a central ramp pressure that may be held for a range of pixel intensities. The ramp function is a CPAP feature that auto-adjusts pressure until the ramp maximum is reached, beyond which the pressure is held constant so that airway is protected from over-inflation.

2.2 Method Overview

Figure 12:
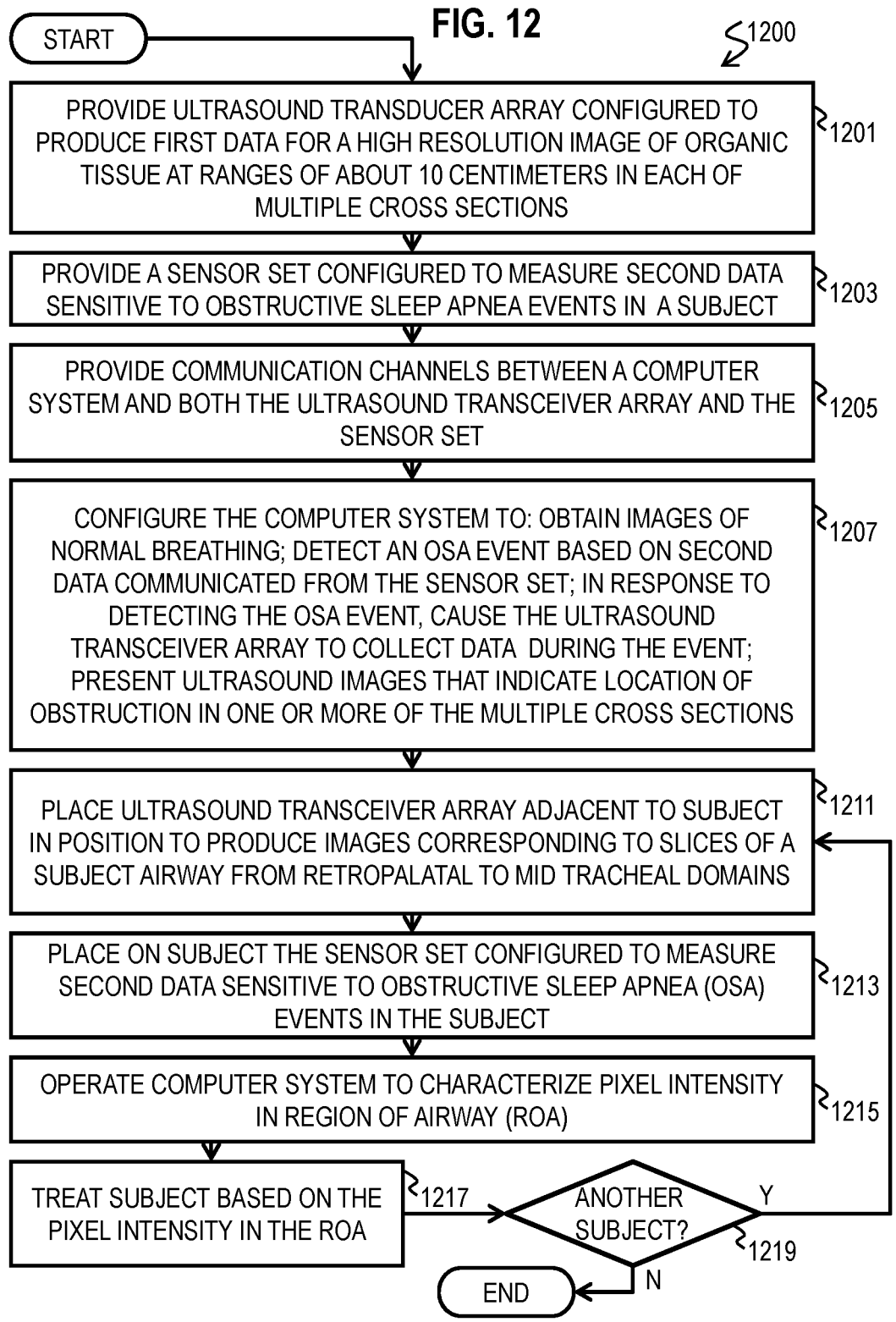
FIG. 12 is a flowchart that illustrates an example method to treat a subject based on automatically determined pixel intensity at a tissue airway interface, according to an embodiment.

FIG. 12 is a flowchart that illustrates an example method to treat a subject based on automatically determined pixel intensity at a tissue airway interface, according to an embodiment. Although steps are depicted in FIG. 12, and in subsequent flowchart FIG. 13, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 1201, an ultrasound transducer array 212 is provided, such as array 310a, and is configured to produce first data (e.g., reflection or transmission temporal profiles along each of multiple beams formed by the array) for a high resolution image (e.g., with a range from about 0.1 to about 2.0 millimeters (mm) of organic tissue at depths into the tissue from about 2 to about 6 cm in each of multiple cross sections (also called slices), e.g., by pointing or sliding or with a 2-D array. Transducer frequencies of 1 to 10 MHz provide an axial resolution from about 0.15 mm to about 1.50 mm. In images, this ranges from about 50 dots per inch (dpi) and above (corresponding to 20 pixels/cm and above). Above about 600 dpi, disadvantages include increase sensor noise and increased demands for storage of data. In experimental embodiments, the airway is at least 3 cm deep. It is advantageous to achieve a depth of penetration of about 5 cm to include the anterior spine. A transducer frequency of about 7 MHz and below is advantageous for providing optimal resolution at the deepest tissues in the region of interest (ROI).

In step 1203, a sensor set 222 is provided, and is configured to measure second data (e.g., blood oxygen saturation, chest movement, breathing sound, among others, or some combination) sensitive to obstructive sleep apnea (OSA) events in a subject.

In step 1205, communication channels 230 are provided between a computer system 240 and both the ultrasound transceiver array 212 and the sensor set 222, either directly or indirectly through command modules 214, 224, respectively.

In step 1207, the computer system 240, including any terminal provided with the transducer array 212, is configured, either by software or special purpose circuitry or some combination, to perform several functions. Those functions include one or more of operating the array to obtain one or more images during normal breathing; detect an OSA event based on second data communicated from the sensor set; in response to detecting the OSA event, cause the ultrasound transceiver array to collect data during the event; and present ultrasound images that indicate location of obstruction in one or more of the multiple cross sections, including storing one or more such images.

In step 1211, the ultrasound transceiver array 212 is placed adjacent to a subject 290 in a position to produce images corresponding to cross sections (slices) of a subject airway from retropalatal to mid tracheal anatomical domains. For example, the ultrasound imaging device 210 (also called an ultrasound probe) is removably attached to the subject with an attachment structure 216 that keeps the array 212 near to, or in contact with, the skin of the subject 290. In some embodiments, step 1211 includes operating the transducer array to collect first data for one or more images that represent corresponding cross-sections in one or more anatomical domains during normal breathing or normal (non OSA event) sleep. In embodiments to monitor an obstruction previously located, the ultrasound transducer array is configured to take successive slices through the location of the obstruction at multiple different times.

In step 1213, the sensor set 222 in placed in position to detect an OSA event in the subject 290. For example, a pulse oximeter is placed on a finger of the subject, and a microphone is placed on the head of the subject. In some embodiments, one or more sensors is configured to automatically alarm, which alarm can be used as a triggering event. For example, some telemetric pulse oximetry probes automatically send an alarm when oxygen saturation falls below a set threshold, such as 90% $SpO_2$. In some embodiments to monitor an obstruction previously located, step 1213 is omitted.

In step 1215, the computer system 240 is operated to present one or more images that indicate a location of an obstruction in the subject, including storing one or more images as image data 252, based on the first data. In some embodiments, the computer system 240 also automatically indicates one or more images, or one or more sub-images (portions of the images), where an obstruction is likely to be indicated. In embodiments to monitor an obstruction previously located, step 1215 includes presenting at each of multiple times, the current CPAP pressure and a measure at the corresponding time of the air-tissue interface strength, such as a number of bright pixels in a mask that marks the air-tissue interface (e.g., the bright pixels in the posterior 40% of FIG. 6L), or the average intensity of pixels from the original image inside the mask, both described above, or some other statistic.

In step 1217, the subject is treated based on the location of an obstruction in an image of the one or more images presented or stored in step 1217. For example, if no obstruction is indicated, the subject is treated for a syndrome other than OSA. If an obstruction is identified and located, then a CPAP titration pressure is determined based on the CPAP pressure that both opens the airway and is considered tolerable by the subject. This step is described in more detail below with reference to FIG. 13. If CPAP is not sufficient, then, in some embodiments, treatment includes a surgical procedure is performed on the subject, e.g., to biopsy or remove a foreign object, if any, or to introduce an object or remove tissue to prevent obstruction at that location by indigenous tissues. In some embodiments, the location of the obstruction is not automatically determined by the computer system; and, a human analyst uses the images presented by the computer system in step 1215, and the human analyst determines the location of an obstruction, if any.

In step 1219, it is determined whether there is another subject to examine. If not, then the method ends. Otherwise, control passes back to step 1211 to place the transducer array on the next subject, and perform the following steps.

Figure 13:
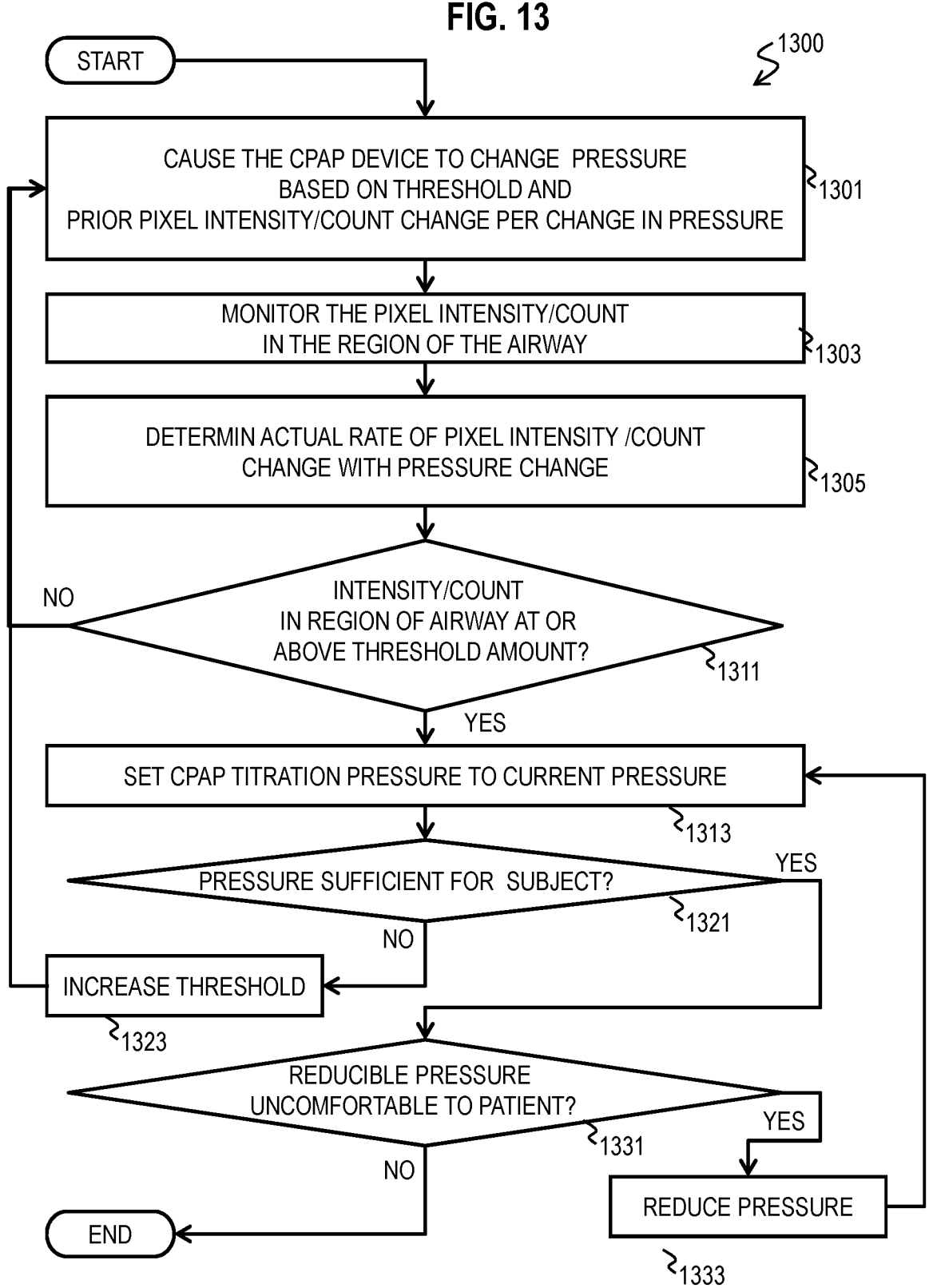
FIG. 13 is a flowchart that illustrates an example method to perform a step of FIG. 12 to determine CPAP titration pressure, according to an embodiment.

FIG. 13 is a flowchart that illustrates an example method 1300 to perform one or more steps of FIG. 12 to determine CPAP titration pressure, according to an embodiment. Thus, method 1300 is an example embodiment of steps 1215 and 1217 of the method 1200 of FIG. 12 if it is determined that airway obstruction is leading to sleep apnea in the subject.

In step 1301, the CPAP device is operated to increase positive driving pressure (Pd) in the airway of the subject, e.g., initially from zero positive pressure (above atmospheric pressure of about 1030 cm of water) to an initial incremental pressure $\Delta P_0$. In general, the new driving pressure at step n+1 is equal to the current driving pressure at step n plus the increment determined for step n $$Pd_{n+1}=Pd_n+\Delta P_n$$

Where $Pd_0=0$. $\Delta P_0$ is determined based on the degree of closing observed in the ultrasound images (e.g., the number of bright pixels in the mask, or the average intensity within the mask, both described above, or some other statistic, e.g., mentioned in Wolf et al., 2015) and some estimate of the rate of ultrasound image change per change in pressure. At first, there may be no knowledge of how this individual subject responds to a change in pressure. In such circumstances a guess or historical value for $\Delta P_0$ may be used. For example, suppose the historical experience across many subjects give a curve as presented in FIG. 10. Because there is a current obstruction at the starting conditions (n=0), it is presumed that the air-tissue interface statistic is low (e.g., mean pixel intensity is low, say 10 gray level units). In this example, the pressure to get to the threshold gray level of 150 units depicted in FIG. 10 is read off the chart, say at 300 cm of water. So in this case $\Delta P_0$ is 300 cm of water.

In step 1303 the pixel intensity or count or other statistic in the region of the airway is monitored under the increased pressure. For example, suppose after the increase of pressure, the mean pixel intensity in the mask is 120.

In step 1305 the pixel intensity or count or other statistic change with pressure is determined to establish the actual responsiveness of the current subject to a CPAP pressure change. For example the change of 110 grey level units with a change of 300 cm of water give a rate of change of 0.37 grey level units per cm of water. This actual rate is used in a subsequent execution of step 1301.

In step 1311, it is determined whether the mean pixel intensity or bright pixel count in the mask or other statistic of the strength of the air-tissue interface in the region of the airway is at or above the threshold amount for that statistic. If not, the airway is considered not sufficiently open and control passes back to step 1301 to change the CPAP driving pressure Pd again. This time, in step 1301, the $\Delta P_n$ will be based on the difference between the current statistic of the strength of the air-tissue interface and the threshold amount as well as the most recent rate of change of the statistic with pressure determined in step 1305. For example, the difference between the threshold mean intensity of grey level 150 units and the actual statistic value 120 gray level units is 30 gray level units. Using the most recent rate of change of 0.37 from step 1305, $\Delta P_1$ is 30/0.37=81 cm H2O, so the new driving pressure, $Pd_1$=381 cm H2O. The steps of 1301, 1303, 1305 and 1311 form a loop that is iterated until the statistic is found in step 1311 to exceed or equal the threshold, each time updating the rate of change of the statistic of the strength of the air-tissue interface with pressure. In some embodiments the rate of change of the statistic value with pressure is assumed a constant and averaged for subsequent use. In the method described, the rate is allowed to change at different levels of airway patency.

If it is determined in step 1311 the mean pixel intensity or bright pixel count in the mask or other statistic of the strength of the air-tissue interface in the region of the airway is at or above the threshold amount for that statistic, then control passes to step 1313. In step 1313, the CPAP titration pressure is set to the current pressure. For example, if a pressure of 381 cm H2O does cause the grey level to exceed 150 units, then in step 1313, the titrated CPAP driving pressure is set to 381 cm H2O. Though the threshold is reached at this pressure, it is not known whether the current subject will reduce the occurrences of sleep apnea events at this threshold, which was predetermined based on other subjects. The following steps are used to determine whether a change in threshold value for the statistic of strength of the air-tissue interface is warranted for the current subject.

In step 1321, it is determined whether the pressure is sufficient for the current subject. For example, the subject is maintained at this pressure for several hours over one or more sleeping sessions; and, the number of sleep apnea events is determined, e.g., based on data from the sensing device 220 or from monitoring of the ultrasound slice through the known obstruction. The pressure is sufficient if the number of events is low enough to satisfy clinical targets, e.g. X events or less in eight hours, where X is chosen in a range from about 1 to bout 5. Currently X=5 events per eight hours is considered clinical cure in the adult population. If not, then the threshold should be increased, and control passes to step 1323.

In step 1323 the threshold is increased. Any method may be used to determine the new threshold. For example, based on historical data that CPAP titration pressures vary among individuals with a mean pressure and a standard deviation that is a fraction of the mean pressure, the change in threshold for the strength of the air-tissue interface could be set based on that fraction, e.g., the threshold could be increased by 25% of that fraction of the original threshold for the strength of the air-tissue interface, or set to the fraction of the pressure change times the most recent rate of change of the statistic per change in pressure, or some combination. In some embodiments, adjustments are made if subject would report sleepiness. It is also possible to measure the inhalation and exhalation volume. For example, if airflow during respiration (patient is exhaling) continues to be below what is considered mean for the population (referred to as tidal volume), then the insufflation pressures are not correct. These are two methods used to titrate CPAP pressures and can be used in conjunction with ultrasonographic estimation to improve accuracy of the system. Control then passes back to step 1301 to increase the CPAP driving pressure based on the new threshold.

If it is determined in step 1321 that the titration pressure is sufficient for the current subject, then control passes to step 1331 to determine whether the titration pressure ought to be reduced. This decision is based on the comfort level of the subject and the amount by which the statistic of strength of the air-tissue interface meets or exceeds the current threshold. If the subject is comfortable with the titration pressure, then the process ends. If the current subject indicates that the current titration pressure is uncomfortable or interferes with sleep, then it is determined whether the titration pressure is reducible. For example, it is determined whether the clinical results exceed the target clinical result or the threshold was exceeded in step 1311. If the titration pressure is not reducible, then the titration pressure is not reduced; and the process ends. However if the subject is uncomfortable and the pressure is reducible, then control passes to step 1333 to reduce the titration pressure for the current subject.

In step 1333 the titration pressure is reduced. Any method may be used to reduce the pressure. In some embodiments, the pressure is reduced by the amount the statistic of strength of the air-tissue interface exceeds the threshold divided by the most recent rate for the change of the statistic with pressure determined in step 1305 or a historical value for the rate based on many prior subjects. In some embodiments, the pressure is reduced by an amount based on an amount by which the time between sleep apnea events exceeds the clinical target for that time. In this embodiment, if the time is exceeded, then the pressure can be reduced by a small decrement, say a small multiple of the pressure resolution of the CPAP device. In some embodiments, the pressure is reduced using a standardized scale to determine if there is clinical benefit. These standardized scales are already in use to screen for sleep apnea, such as the Epworth sleepiness scale. The advantages of this approach include ease of use, inexpensive, rapid. A disadvantage of this approach is lack of objectivity. IN some embodiments, the pressure is reduced based on calibration achieved using concurrent polysomnography (sleep study). Currently, it is possible to do a sleep study while the patient is being fitted with a CPAP machine to assess response to therapy. An advantage of this approach is gold standard of objective assessment. Disadvantages include involving a concurrent sleep study which entails admission to a facility, many hours of time and high expense. Control then passes back to step 1313 and following step, to reset the CPAP titration pressure to the lower pressure and determine whether the new reduced pressure is still sufficient.

3. COMPUTATIONAL HARDWARE OVERVIEW

Figure 14:
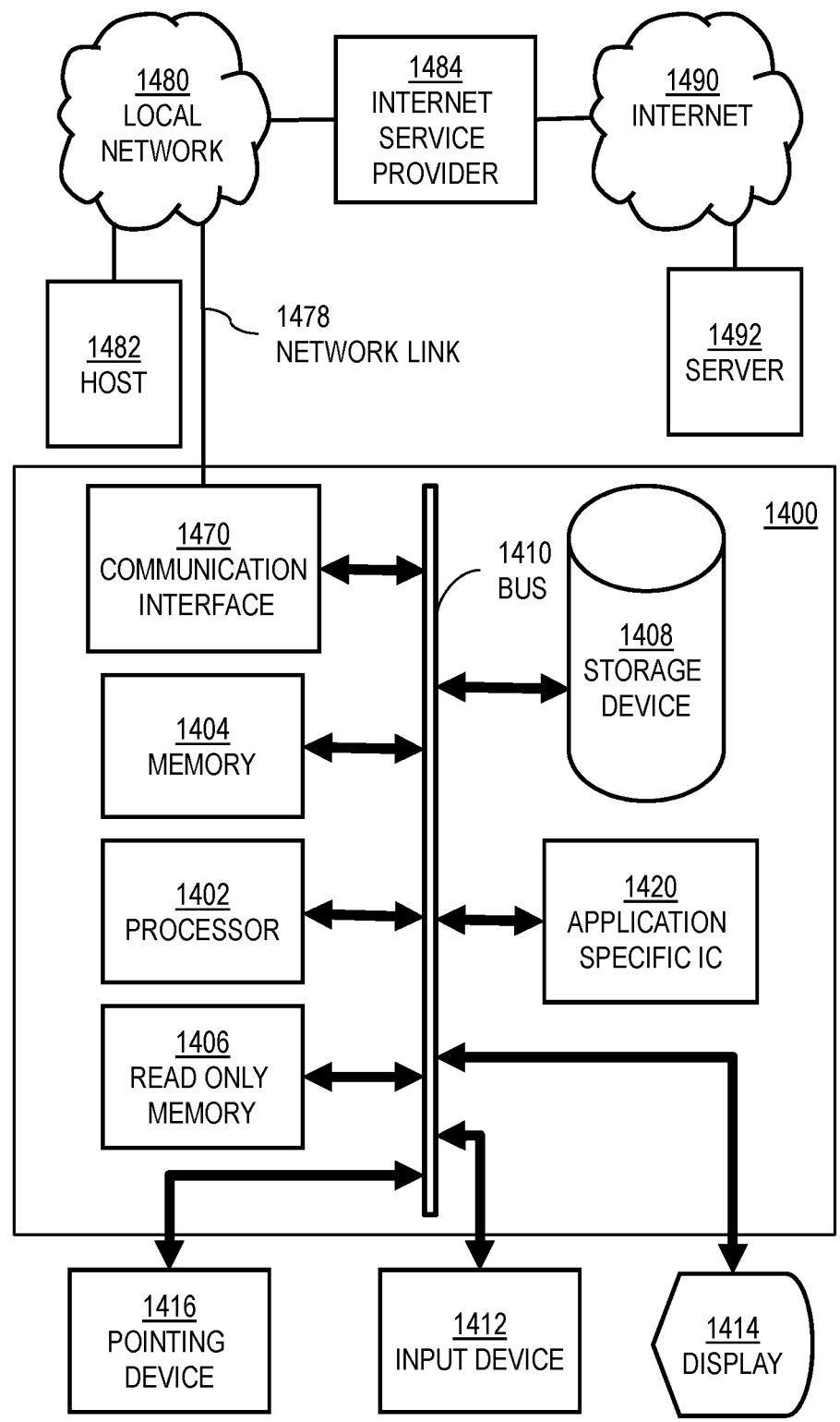
FIG. 14 is a block diagram that illustrates a computer system upon which an embodiment of the invention may be implemented.

FIG. 14 is a block diagram that illustrates a computer system 1400 upon which an embodiment of the invention may be implemented. Computer system 1400 includes a communication mechanism such as a bus 1410 for passing information between other internal and external components of the computer system 1400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1400, or a portion thereof, constitutes a means for performing one or more steps of one or more methods described herein.

A sequence of binary digits constitutes digital data that is used to represent a number or code for a character. A bus 1410 includes many parallel conductors of information so that information is transferred quickly among devices coupled to the bus 1410. One or more processors 1402 for processing information are coupled with the bus 1410. A processor 1402 performs a set of operations on information. The set of operations include bringing information in from the bus 1410 and placing information on the bus 1410. The set of operations also typically include comparing two or more units of information, shifting positions of units of information, and combining two or more units of information, such as by addition or multiplication. A sequence of operations to be executed by the processor 1402 constitutes computer instructions.

Computer system 1400 also includes a memory 1404 coupled to bus 1410. The memory 1404, such as a random access memory (RAM) or other dynamic storage device, stores information including computer instructions. Dynamic memory allows information stored therein to be changed by the computer system 1400. RAM allows a unit of information stored at a location called a memory address to be stored and retrieved independently of information at neighboring addresses. The memory 1404 is also used by the processor 1402 to store temporary values during execution of computer instructions. The computer system 1400 also includes a read only memory (ROM) 1406 or other static storage device coupled to the bus 1410 for storing static information, including instructions, that is not changed by the computer system 1400. Also coupled to bus 1410 is a non-volatile (persistent) storage device 1408, such as a magnetic disk or optical disk, for storing information, including instructions, that persists even when the computer system 1400 is turned off or otherwise loses power.

Information, including instructions, is provided to the bus 1410 for use by the processor from an external input device 1412, such as a keyboard containing alphanumeric keys operated by a human user, or a sensor. A sensor detects conditions in its vicinity and transforms those detections into signals compatible with the signals used to represent information in computer system 1400. Other external devices coupled to bus 1410, used primarily for interacting with humans, include a display device 1414, such as a cathode ray tube (CRT) or a liquid crystal display (LCD), for presenting images, and a pointing device 1416, such as a mouse or a trackball or cursor direction keys, for controlling a position of a small cursor image presented on the display 1414 and issuing commands associated with graphical elements presented on the display 1414.

In the illustrated embodiment, special purpose hardware, such as an application specific integrated circuit (IC) 1420, is coupled to bus 1410. The special purpose hardware is configured to perform operations not performed by processor 1402 quickly enough for special purposes. Examples of application specific ICs include graphics accelerator cards for generating images for display 1414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1400 also includes one or more instances of a communications interface 1470 coupled to bus 1410. Communication interface 1470 provides a two-way communication coupling to a variety of external devices that operate with their own processors, such as printers, scanners and external disks. In general the coupling is with a network link 1478 that is connected to a local network 1480 to which a variety of external devices with their own processors are connected. For example, communication interface 1470 may be a parallel port or a serial port or a universal serial bus (USB) port on a personal computer. In some embodiments, communications interface 1470 is an integrated services digital network (ISDN) card or a digital subscriber line (DSL) card or a telephone modem that provides an information communication connection to a corresponding type of telephone line. In some embodiments, a communication interface 1470 is a cable modem that converts signals on bus 1410 into signals for a communication connection over a coaxial cable or into optical signals for a communication connection over a fiber optic cable. As another example, communications interface 1470 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1470 sends and receives electrical, acoustic or electromagnetic signals, including infrared and optical signals, that carry information streams, such as digital data.

The term computer-readable medium is used herein to refer to any medium that participates in providing information to processor 1402, including instructions for execution. Such a medium may take many forms, including, but not limited to, non-volatile media, volatile media and transmission media. Non-volatile media include, for example, optical or magnetic disks, such as storage device 1408. Volatile media include, for example, dynamic memory 1404. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1402, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1402, except for carrier waves and other signals.

Logic encoded in one or more tangible media includes one or both of processor instructions on a computer-readable storage media and special purpose hardware, such as ASIC 1420.

Network link 1478 typically provides information communication through one or more networks to other devices that use or process the information. For example, network link 1478 may provide a connection through local network 1480 to a host computer 1482 or to equipment 1484 operated by an Internet Service Provider (ISP). ISP equipment 1484 in turn provides data communication services through the public, world-wide packet-switching communication network of networks now commonly referred to as the Internet 1490. A computer called a server 1492 connected to the Internet provides a service in response to information received over the Internet. For example, server 1492 provides information representing video data for presentation at display 1414.

The invention is related to the use of computer system 1400 for implementing the techniques described herein. According to one embodiment of the invention, those techniques are performed by computer system 1400 in response to processor 1402 executing one or more sequences of one or more instructions contained in memory 1404. Such instructions, also called software and program code, may be read into memory 1404 from another computer-readable medium such as storage device 1408. Execution of the sequences of instructions contained in memory 1404 causes processor 1402 to perform the method steps described herein. In alternative embodiments, hardware, such as application specific integrated circuit 1420, may be used in place of or in combination with software to implement the invention. Thus, embodiments of the invention are not limited to any specific combination of hardware and software.

The signals transmitted over network link 1478 and other networks through communications interface 1470, carry information to and from computer system 1400. Computer system 1400 can send and receive information, including program code, through the networks 1480, 1490 among others, through network link 1478 and communications interface 1470. In an example using the Internet 1490, a server 1492 transmits program code for a particular application, requested by a message sent from computer 1400, through Internet 1490, ISP equipment 1484, local network 1480 and communications interface 1470. The received code may be executed by processor 1402 as it is received, or may be stored in storage device 1408 or other non-volatile storage for later execution, or both. In this manner, computer system 1400 may obtain application program code in the form of a signal on a carrier wave.

Various forms of computer readable media may be involved in carrying one or more sequence of instructions or data or both to processor 1402 for execution. For example, instructions and data may initially be carried on a magnetic disk of a remote computer such as host 1482. The remote computer loads the instructions and data into its dynamic memory and sends the instructions and data over a telephone line using a modem. A modem local to the computer system 1400 receives the instructions and data on a telephone line and uses an infra-red transmitter to convert the instructions and data to a signal on an infra-red a carrier wave serving as the network link 1478. An infrared detector serving as communications interface 1470 receives the instructions and data carried in the infrared signal and places information representing the instructions and data onto bus 1410. Bus 1410 carries the information to memory 1404 from which processor 1402 retrieves and executes the instructions using some of the data sent with the instructions. The instructions and data received in memory 1404 may optionally be stored on storage device 1408, either before or after execution by the processor 1402.

Figure 15:
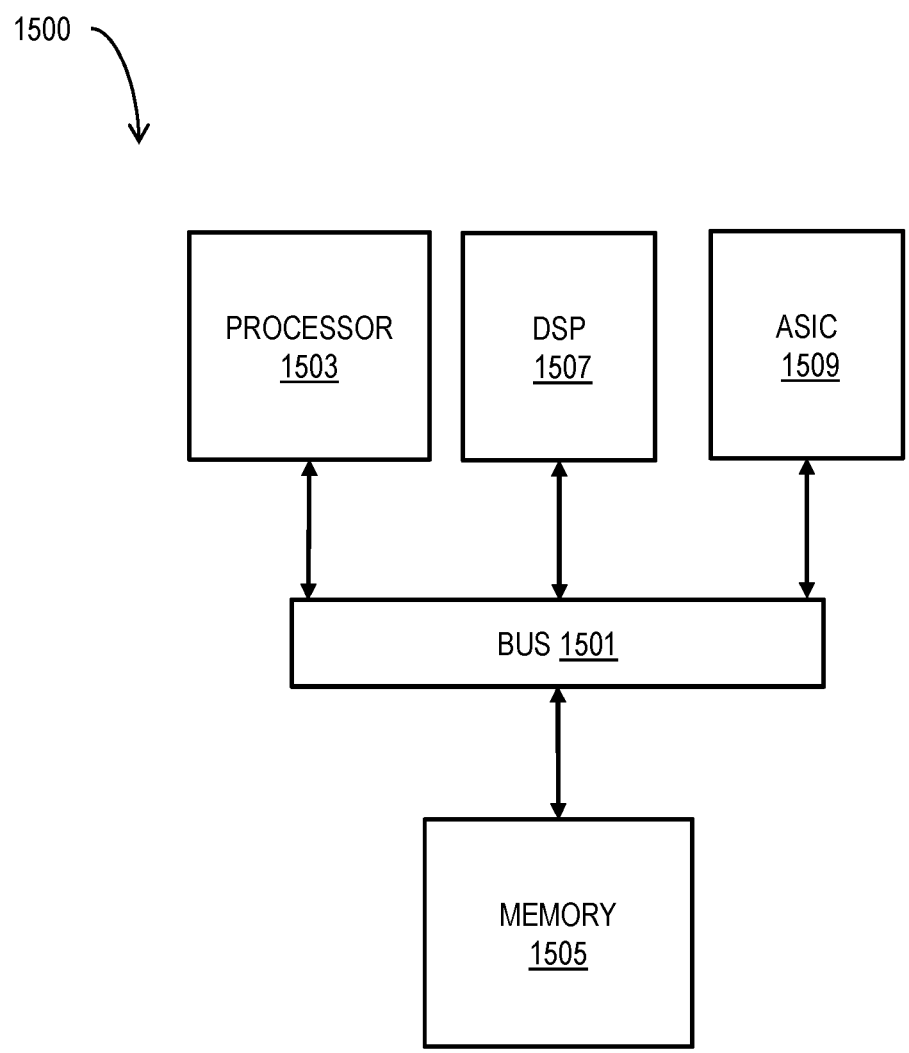
FIG. 15 illustrates a chip set upon which an embodiment of the invention may be implemented.

FIG. 15 illustrates a chip set 1500 upon which an embodiment of the invention may be implemented. Chip set 1500 is programmed to perform one or more steps of a method described herein and includes, for instance, the processor and memory components described with respect to FIG. 14 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1500, or a portion thereof, constitutes a means for performing one or more steps of a method described herein.

In one embodiment, the chip set 1500 includes a communication mechanism such as a bus 1501 for passing information among the components of the chip set 1500. A processor 1503 has connectivity to the bus 1501 to execute instructions and process information stored in, for example, a memory 1505. The processor 1503 may include one or more processing cores with each core configured to perform independently. A multi-core processor enables multiprocessing within a single physical package. Examples of a multi-core processor include two, four, eight, or greater numbers of processing cores. Alternatively or in addition, the processor 1503 may include one or more microprocessors configured in tandem via the bus 1501 to enable independent execution of instructions, pipelining, and multithreading. The processor 1503 may also be accompanied with one or more specialized components to perform certain processing functions and tasks such as one or more digital signal processors (DSP) 1507, or one or more application-specific integrated circuits (ASIC) 1509. A DSP 1507 typically is configured to process real-world signals (e.g., sound) in real time independently of the processor 1503. Similarly, an ASIC 1509 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1503 and accompanying components have connectivity to the memory 1505 via the bus 1501. The memory 1505 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1505 also stores the data associated with or generated by the execution of one or more steps of the methods described herein.

4. ALTERNATIVES, VARIATIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus a range from 0 to 10 includes the range 1 to 4 in some embodiments.

5. REFERENCES

The contents of each of the following references are hereby incorporated by reference as if fully set forth herein except for terminology that is inconsistent with that used herein.

Bhattacharyya, N., Blake, S. P. & Fried, M. P. 2000. Assessment of the airway in obstructive sleep apnea syndrome with 3-dimensional airway computed tomography. Otolaryngology-Head and Neck Surgery 123: 444-449.

Chaban, R., Cole, P. & Hoffstein, V. 1988. Site of upper airway obstruction in subjects with idiopathic obstructive sleep apnea. Laryngoscope 98: 641-647.

Clement, G., White, J. & Hynynen, K. 2000. Investigation of a large-area phased array for focused ultrasound surgery through the skull. Physics in Medicine and Biology 45, 1071.

Collop, N., Anderson, W. M., Boehlecke, B., Claman, D., Goldberg, R., Gottlieb, D. J., Hudgel, D., Sataia, M., & Schwab, R. 2007. Clinical guidelines for the use of unattended portable monitors in the diagnosis of obstructive sleep apnea in adult subjects. J Clin Sleep Med 3: 737-747.

Crane, J. P., LeFevre, M. L., Winborn, R. C., Evans, J. K., Ewigman, B. G., Bain, R. P., Frigoletto, F. D., McNellis, D., & RADIUS Study Group. 1994. A randomized trial of prenatal ultrasonographic screening: impact on the detection, management, and outcome of anomalous fetuses. Am J Obstetrics and Gynecology 171: 392.

Croft, C. & Pringle, M. 1991. Sleep nasendoscopy: a technique of assessment in snoring and obstructive sleep apnoea. Clinical Otolaryngology & Allied Sciences 16: 504-509.

Deberry-Borowiecki, B., Kukwa, A. & Blanks, R. H. 1988. Cephalometric analysis for diagnosis and treatment of obstructive sleep apnea. Laryngoscope 98: 226-234.

Ezri, T., Gewürtz, G., Sessler, D. I., Medalion, B., Szmuk, P., Hagberg, C., & Susmallian, S. 2003. Prediction of difficult laryngoscopy in obese subjects by ultrasound quantification of anterior neck soft tissue. Anaesthesia 58: 1111-1114.

Findley, L., Barth J. T., Powers D. C., Wilhoit S. C., Boyd D. G. & Suratt P. M. 1986. Cognitive impairment in subjects with obstructive sleep apnea and associated hypoxemia. Chest 90(5): 686-690.

Flemons, W. W. 2002. Obstructive sleep apnea. New England Journal of Medicine 347: 498-504.

Gardin, J. M., FASE, M. G.-H., Jaff, M. & Mohler, E. 2006. Clinical application of noninvasive vascular ultrasound in cardiovascular risk stratification: a report from the American Society of Echocardiography and the Society of Vascular Medicine and Biology. J Am Soc Echocardiogr 19: 943-954.

Girard, E. E. 2003. Automated Detection of Obstructive Sleep Apnea Using Ultrasound Imaging. Charlottesville, Va.: University of Virginia.

Guilleminault, C., Connolly, S. J. & Winkle, R. A. 1983. Cardiac arrhythmia and conduction disturbances during sleep in 400 subjects with sleep apnea syndrome. American J Cardio 52: 490-494.

Guilleminault, C., Riley, R. & Powell, N. 1984. Obstructive sleep apnea and abnormal cephalometric measurements. Implications for treatment. Chest 86: 793-794.

Hamers, R., Bruining, N., Knook, M., Sabate, M. & Roelandt, J. 2001. A Novel Approach to Quantitative Analysis of Intra Vascular Ultrasound Images. In: Computers in Cardiology. IEEE: 589-592.

Hoskins, P. R., Martin, K. & Thrush, A. 2010. Diagnostic ultrasound: physics and equipment. Cambridge, U.K.: Cambridge University Press.

Hudgel, D. W. 1986. Variable site of airway narrowing among obstructive sleep apnea subjects. J Applied Physiology 61: 1403-1409.

Hung, J., Whitford, E., Hillman, D. & Parsons, R. Association of sleep apnoea with myocardial infarction in men. 1990. Lancet 336: 261-264.

Johns, M. W. 1993. Daytime sleepiness, snoring, and obstructive sleep apnea: The Epworth Sleepiness Scale. Chest 103(1): 30-36.

Kajekar, P., Mendonca, C. & Gaur, V. 2010. Role of Ultrasound in Airway Assessment and Management. International J Ultrasound & Applied Technologies in Perioperative Care 1: 97-100.

Kuratli, C. & Huang, Q. 2000. A CMOS ultrasound rangefinder microsystem. IEEE Journal of Solid-State Circuits 35: 2005-2017.

Marin, J. M., Carrizo, S. J., Vicente, E. & Agusti, A. G. 2005. Long-term cardiovascular outcomes in men with obstructive sleep apnoea-hypopnoea with or without treatment with continuous positive airway pressure: an observational study. Lancet 365: 1046-1053.

McNay, M. B. & Fleming, J. E. 1999. Forty years of obstetric ultrasound 1957-1997: From A-scope to three dimensions. Ultrasound in Medicine and Biology 25: 3-56.

Morrison, D., Launois, S. H., Isono, S., Feroah, T. R., Whitelaw, W. A., & Remmers, J. E. 1993. Pharyngeal narrowing and closing pressures in subjects with obstructive sleep apnea. American J Respiratory and Critical Care Medicine 148(3): 606-611.

Muthukumaran, S., Yang, K., Seuren, A., Kentish, S., Ashokkumar, M., Stevens, G. W., & Grieser, F. 2004. The use of ultrasonic cleaning for ultrafiltration membranes in the dairy industry. Separation and purification technology 39, 99-107.

Pepin, J., Ferretti, G., Veale, D., Romand, P., Coulomb, M., Brambilla, C., & Lévy, P. A. 1992. Somnofluoroscopy, computed tomography, and cephalometry in the assessment of the airway in obstructive sleep apnoea. Thorax 47(3): 150-156.

Riley, R., Guilleminault, C., Powell, N. & Simmons, F. 1985. Palatopharyngoplasty failure, cephalometric roentgenograms, and obstructive sleep apnea. Otolaryngology-Head and Neck Surgery 93: 240.

Riley, R. W., Powell, N. B. & Guilleminault, C. 1993. Obstructive sleep apnea syndrome: a review of 306 consecutively treated surgical subjects. Otolaryngology-Head and Neck Surgery 108: 117.

Rodenstein, D., Dooms, G., Thomas, Y., Liistro, G., Stanescu, D. C., Culee, C., & Aubert-Tulkens, G. 1990. Pharyngeal shape and dimensions in healthy subjects, snorers, and subjects with obstructive sleep apnoea. Thorax 45(10): 722-727.

Romero, R. Routine obstetric ultrasound. 2003. Ultrasound in Obstetrics & Gynecology 3: 303-307.

Ruecroft, G., Hipkiss, D., Ly, T., Maxted, N. & Cains, P. W. 2005. Sonocrystallization: the use of ultrasound for improved industrial crystallization. Organic process research & development 9: 923-932.

Schwab, R. J., Pasirstein, M., Pierson, R., Mackley, A., Hachadoorian, R., Arens, R., Maislin, G., & Pack, A. I. 2003. Identification of upper airway anatomic risk factors for obstructive sleep apnea with volumetric magnetic resonance imaging. American J Respiratory and Critical Care Medicine 168(5): 522-530.

Shamsuzzaman, A. S., Gersh, B. J. & Somers, V. K. 2003. Obstructive sleep apnea. JAMA: the journal of the American Medical Association 290: 1906-1914.

Shelton, K. E., Woodson, H., Gay, S. & Suratt, P. M. 1993. Pharyngeal fat in obstructive sleep apnea. American Journal of Respiratory and Critical Care Medicine 148: 462-466.

Shepard, J. W. & Thawley, S. E. 1990. Localization of upper airway collapse during sleep in subjects with obstructive sleep apnea. American Journal of Respiratory and Critical Care Medicine 141: 1350-1355.

Siegel, H., Sonies, B. C., Graham, B., McCutchen, C., Hunter, K., Vega-Bermudez, F., & Sato, S. 2000. Obstructive sleep apnea: A study by simultaneous polysomnography and ultrasonic imaging. Neurology 54: 1872-1872.

Silk, M. G. 1984. Ultrasonic transducers for nondestructive testing. London: Taylor & Francis.

Smith, S., Trahey, G. & Von Ramm, O. 1986. Phased array ultrasound imaging through planar tissue layers. Ultrasound in Medicine & Biology 12: 229-243.

Strollo Jr, P. J. & Rogers, R. M. 1996. Obstructive sleep apnea. New England Journal of Medicine 334: 99-104.

Teran-Santos, J., Jimenez-Gomez, A. & Cordero-Guevara, J. 1999. The association between sleep apnea and the risk of traffic accidents. New England J Med 340: 847-851.

Veasey, S. C., Guilleminault, C., Strohl, K. P., Sanders, M. H., Ballard, R. D., & Magalang, U. J. 2006. Medical therapy for obstructive sleep apnea: a review by the Medical Therapy for Obstructive Sleep Apnea Task Force of the Standards of Practice Committee of the American Academy of Sleep Medicine. Sleep 29(8): 1036.

Wolf, J., & Isaiah, A., 2015, U.S. Patent Application Publication No. US2015/0209001.

What is claimed is:

1. A method implemented on a processor comprising:
   automatically receiving a first plurality of ultrasound images representing a cross sections of an airway in a neck of a subject obtained by an ultrasound transducer array directed toward the subject at a corresponding plurality of different times;
   determining a region of interest comprising a subset of pixels of each image of the first plurality of ultrasound images, wherein each region of interest encompasses an airway of the subject;
   for each of the plurality of images, automatically forming a mask of pixels associated with an air-tissue interface based on both a morphological opening and a morphological closing with a structural element in the region of interest if the mask includes at least a minimum number of pixels;
   for each of the plurality of images, automatically determining a value of a statistic of pixels within the mask;
   presenting on an display device output data that indicates a degree of airway patency proportional to the value of the statistic at each of the corresponding plurality of different times.

2. A method as recited in claim 1, wherein the statistic is mean intensity value within the mask.

3. A method as recited in claim 1, wherein the statistic is a number of pixels within the mask.

4. A method as recited in claim 1, wherein the statistic is a number of pixels having an intensity above a minimum intensity within the mask.

5. A method as recited in claim 1, wherein the minimum number of pixels is 20.

6. A method as recited in claim 1, wherein the structural element is diamond shaped.

7. A computer-readable medium carrying one or more sequences of instructions, wherein execution of the one or more sequences of instructions by one or more processors causes the one or more processors to perform the steps of:
   automatically receiving a first plurality of ultrasound images representing a cross sections of an airway in a neck of a subject obtained by an ultrasound transducer array directed toward the subject at a corresponding plurality of different times;
   determining a region of interest comprising a subset of pixels of each image of the first plurality of ultrasound images, wherein each region of interest encompasses an airway of the subject;
   for each of the plurality of images, automatically forming a mask of pixels associated with an air-tissue interface based on both a morphological opening and a morphological closing with a structural element in the region of interest if the mask at least a minimum number of pixels;
   for each of the plurality of images, automatically determining a value of a statistic of pixels within the mask;
   presenting on an display device output data that indicates a degree of airway patency proportional to the value of the statistic at each of the corresponding plurality of different times.

8. A system comprising:
   at least one processor; and
   at least one computer-readable medium including one or more sequences of instructions,
   the at least one computer-readable medium and the one or more sequences of instructions configured to, with the at least one processor, cause the system to perform at least the following,
   automatically receiving a first plurality of ultrasound images representing a cross sections of an airway in a neck of a subject obtained by an ultrasound transducer array directed toward the subject at a corresponding plurality of different times;
   determining a region of interest comprising a subset of pixels of each image of the first plurality of ultrasound images, wherein each region of interest encompasses an airway of the subject;
   for each of the plurality of images, automatically forming a mask of pixels associated with an air-tissue interface based on both a morphological opening and a morphological closing with a structural element in the region of interest if the mask at least a minimum number of pixels;

for each of the plurality of images, automatically determining a value of a statistic of pixels within the mask;

presenting on an display device output data that indicates a degree of airway patency proportional to the value of the statistic at each of the corresponding plurality of different times.

\* \* \* \* \*